United States Patent
Duvick et al.

(10) Patent No.: US 6,433,249 B1
(45) Date of Patent: Aug. 13, 2002

(54) USE OF β-GLUCOSIDASE TO ENHANCE DISEASE RESISTANCE AND RESISTANCE TO INSECTS IN CROP PLANTS

(75) Inventors: Jon Duvick; Carl R. Simmons, both of Des Moines, IA (US); Oswald R. Crasta, Branford; Otto Folkerts, Guilford, both of CT (US)

(73) Assignees: Pioneer Hi-Bred International, Inc., Des Moines, IA (US); CuraGen Corporation, New Haven, CT (US)

( * ) Notice: Subject to any disclaimer, the term of this patent is extended or adjusted under 35 U.S.C. 154(b) by 0 days.

(21) Appl. No.: 09/431,470

(22) Filed: Nov. 1, 1999

Related U.S. Application Data

(60) Provisional application No. 60/107,920, filed on Nov. 10, 1998.

(51) Int. Cl.$^7$ .............................. A01H 1/00; A01H 5/00; C12N 15/82; C12N 15/29; C12N 15/56; C12N 5/04

(52) U.S. Cl. ...................... 800/279; 800/287; 800/298; 800/301; 800/320.1; 435/200; 435/418; 435/419; 435/412

(58) Field of Search ................................ 435/69.1, 207, 435/209, 412, 410, 418, 419, 320.1, 468; 800/279, 298, 301, 302, 320.1, 287; 536/23.2, 23.6, 23.7, 23.74

(56) References Cited

U.S. PATENT DOCUMENTS

| | | |
|---|---|---|
| 5,767,369 A | 6/1998 | Ryals et al. |
| 5,973,228 A | 10/1999 | Carlson et al. |

FOREIGN PATENT DOCUMENTS

| | | |
|---|---|---|
| WO | WO 94/16077 | 7/1994 |
| WO | WO 98/05760 | 2/1998 |
| WO | WO 98/11235 | 3/1998 |

OTHER PUBLICATIONS

Yuan, L. and Knauf, V.C., "Modification of plant components." 1997, Current Opinion in Biotechnology, vol. 8, pp. 227–233.*

Zhu et al. Enhanced protection against fungal attack by constitutive co–expression of chitinase and glucanase genes in transgenic tobacco. BIO/Technology 12:807–812. 1994.*

Hall et al. Plant Cell Structure and Metabolism. Longman Group Limited. London England. 1974. p. 356.*

Haug and Larsen. Biosynthesis of Algal Polysaccharides IN Plant Carbohydrate Biochemistry. editor J.B. Pridham. Academic Press. New York, NY. 1974. pp. 207–208.*

Simmons et al. "Maize rhm1 Resistance to *Biopolaris maydis* Is Associated with Few Differences in Pathogenesis–Related Proteins and Global mRNA Profiles" MPMI 137–00, manuscript accepted Mar. 30, 2001.

Brzobohaty et al. (1993) "Release of Active Cytokinin by a β–Glucosidase Localized to the Maize Root Meristem," *Science* 262:1051–1054.

Gus–Mayer et al. (1998) "Local mechanical stimulation induces components of the pathogen defense response in parsley," *Proc. Natl. Acad. Sci. USA* 95:8398–8403, Plant Biology.

Gus–Mayer et al. (1994) "The amino acid sequence previously attributed to a protein kinase or a TCP1–related molecular chaperone and co–purified with phytochrome is a β–glucosidase," *FEBS Letters* 347:51–54, Federation of European Biochemical Societies.

Shukla et al. (1988) "Biochemical studies on response of tobacco and tomato plants to root knot nematode infection," *Tob. Res.* 14 (1): 43–50, Gujarat Agricultural University, Anand Campus.

Hopke et al. (1994) "Herbivore–Induced Volatiles: The Emission of Acyclic Homoterpenes From Leaves of *Phaseolus lunatus* and *Zeal mays* Can Be Triggered By A β–Glucosidase and Jasmonic Acid", *FEBS Letters* 352:146–150.

Esen et al. (1991) "pH–and Temperature–Dependent β–Glucosidase Multiplicity in Maize (Zea mays L. ) Is A Proteolysis Artifact", *Plant Science* 74:17–26.

Seo et al. (1995) "Induction of Salicylic Acid β–Glucosidase in Tobacco Leaves by Exogenous Salicylic Acid", *Plant Cell Physiol.* 36(3):447–453.

Cuevas et al. (1992) "Partial Purification and Characterization of aHydroxamic Acid Glucoside β–D–Glucosidase From Maize", *Phytochemistry* 31(8):2609–2612.

Ito et al. (1995) "Percursors of Antifungal Substances from Cherry Leaves (*Prunus yedoensis* Matsumura)", *Biosci. Biotech. Biochem.* 59(10):1944–1945.

Russell et al. (1992) "Protein Synthesis in Maize During Anaerobic and Heat Stress", *Plant Physiol.* 99:615–620.

Esen (1992) "β–Glucosidases Biochemistry and Molecular Biology", American Chemical Society Symposium Series 533, Chapter, 1, Developed from a Symposium sponsored by the Division of Agricultural and Food Chemistry at the 204$^{th}$ National Meeting of the American Chemical Society, Washington, DC, Aug. 23–28, 1992, pp. 1–14.

Chen et al. (1995) "Induction, Modification, andTransduction of the Salicylic Acid Signal in Plant Defense Responses" *Proc. Natl. Acad. Sci. USA* 92:4134–4137.

Frova (1994) "Tissue Specificity and Genetic Control of the β–Glu null Phenotype in Maize", *Plant Science* 102:171–180.

Babcock et al. (1994) "Substrate Specificity of Maize β–Glucosidase", *Plant Science* 101:31–39.

* cited by examiner

*Primary Examiner*—David T. Fox
*Assistant Examiner*—David H Kruse
(74) *Attorney, Agent, or Firm*—Alston & Bird LLP

(57) ABSTRACT

Methods for the enhancement of plant disease resistance are provided. The methods comprise transforming said plant with a gene encoding β-glucosidase and increasing the expression said gene above wild-type levels. Transformed plants, plant cells and seeds are provided. Disease resistant transformed plants, plant cells and seeds are also provided.

84 Claims, 3 Drawing Sheets

*rhm1* NOT DIFFERENT IN GENERAL DEFENSE GENE EXPRESSION POSTURE

| | WT 865 JOB 4795 | *rhm1* 865 JOB 4613 | WT 1004 JOB 4796 | *rhm1* 1004 JOB 4614 | ALL N-FOLD AVE |
|---|---|---|---|---|---|
| UP-REGULATED | SUM= 358.1 AVE= 2.84 N= 126 | SUM= 349.4 AVE= 2.77 N= 126 | SUM= 406.2 AVE= 3.22 N= 126 | SUM= 415.3 AVE= 3.30 N= 126 | SUM= 390.1 AVE= 3.10 N= 126 |
| DOWN-REGULATED | SUM= -82.6 AVE= -2.36 N= 35 | SUM= -77.7 AVE= -2.22 N= 35 | SUM= -82.0 AVE= -2.34 N= 35 | SUM= -83.3 AVE= -2.38 N= 35 | SUM= -82.1 AVE= -2.35 N= 35 |

FIG. 1.

USE OF β-GLUCOSIDASE TO ENHANCE DISEASE RESISTANCE AND RESISTANCE TO INSECTS IN CROP PLANTS

CROSS-REFERENCE TO RELATED APPLICATION

This application claims the benefit of U.S. Provisional Application No. 60/107,920 filed Nov. 10, 1998.

FIELD OF THE INVENTION

The invention is drawn to the genetic manipulation of plants, particularly to enhancing pathogen resistance in plants.

BACKGROUND OF THE INVENTION

Plant pests result in losses to farmers which run into millions of dollars per year. The rising costs of pesticides, the increasing resistance of insects to pesticides, and their undesirable effects on the environment, stresses the need to exploit host plant resistance to pests and diseases. In the past, pathogen disease resistance was handled by conventional crop breeding, which while sophisticated is time consuming and expensive. While various "genetic engineering" strategies for enhancing pathogen resistance have been proposed, and some are showing success, the record has been spotty and no single general strategy has emerged that bears consistent success. In fact, there may not be a single strategy that will work against all pathogens, or that will work in all plants given the evolutionary dynamics of plants and pathogens. Providing seed producers and growers with a variety of weapons to choose from is to their advantage. Thus, additional mechanisms are needed to protect plants against plant pests.

β-glucosidases catalyze the hydrolysis of glycosidic linkages in aryl and alkyl β-glucosides and cellobiose and occur ubiquitously in plants, fungi, animals and bacteria. Maize β-glucosidase is an abundant soluble protein in young, growing plant parts. In seedlings, β-glucosidase activity has been found mainly in coleoptiles and mesocotyls and, to a lesser extent, in roots. One physiological function for maize β-glucosidase is the hydrolysis of the hydroxamic acid glucoside (for example 2,4-dihydroxy-7-methoxy-1,4-benzoxazine-3-one glucoside DIMBOA-glc=DIMBOA glucoside). The hydrolysis reaction releases a biologically active free form of the compound from its conjugated form.

Hydroxamic acids derived from 4-hydroxy-1,4-benzoxazin-3-one are secondary compounds produced in cereals such as maize, wheat and rye, and in other Gramineae. Upon disruption of the tissue, hydroxamic acids are liberated which are chemically labile and of higher toxicity than the parent glucosides. Hydroxamic acids play a major role in the defense of the plant against insects such as the European corn borer, *Ostrinia nubilalis*, the western corn root worm, *Diabrotica virgifera*, and cereal aphids and pathogens such as corn leaf blight (Helmintho sporium) and stalk rot (Diplodia magdis). The concentrations of hydroxamic acids in a given tissue of the plant and in the plant as a whole decrease as the tissue or plant age, thereby rendering the plant more susceptible to pathogen attack. β-d-glucohydrolysis is catalyzed by β-glucosidase, and therefore may be a decisive factor in regulating the concentration of hydroxamic acids and thereby promoting plant pathogen resistance.

SUMMARY OF THE INVENTION

Methods for enhancing disease resistance of plant cells and plants are provided. The methods comprise transforming a plant cell with a DNA construct comprising a promoter operably linked to a nucleotide sequence encoding a β-glucosidase. Methods provide for increased expression of the β-glucosidase sequence in the plant, thereby providing enhanced disease resistance. The β-glucosidase coding sequence may be expressed utilizing various promoters to control the tissue or temporal specificity of the protein in the transformed plant.

Transformed plants, plant cells, and tissues, having altered β-glucosidase levels are also provided. Such plants exhibit increased pathogen and disease resistance.

BRIEF DESCRIPTION OF THE DRAWINGS

FIG. 1 provides the levels of mRNA present in independent rhm1 alleles and their corresponding wildtype siblings using CuraGen mRNA profiling technology. The number of CuraGen Bands (mRNA fragments) showing expression changes greater than plus or minus 1.4 fold is designated as 'N'. 865 and 1004 denote two alleles of rhm1 and the corresponding wildtype siblings. Sum is the total addition of fold expression differences for all CuraGen Bands (N). The average is the sum divided by N.

DETAILED DESCRIPTION OF THE INVENTION

Figure 2:
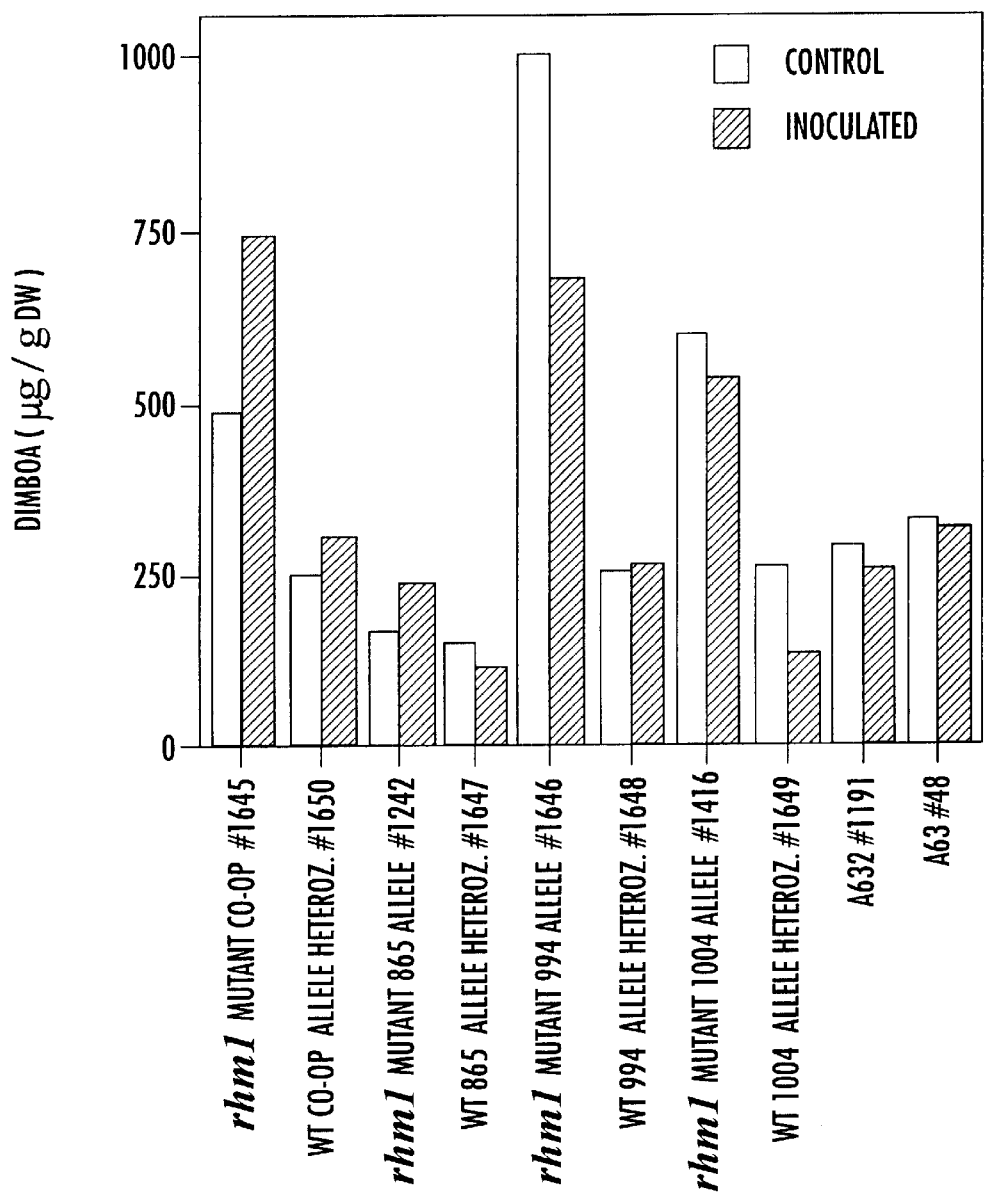
FIG. 2 provides data showing higher levels of free DIMBOA in alleles of rhm1 relative to wildtype heterozygote siblings.

Compositions and methods are provided for the utilization of the gene encoding β-glucosidase to enhance plant disease resistance. In particular, the β-glucosidase sequence finds use in modulating the levels of β-glucosidase in a transformed plant cell. The method involves transforming a plant with a gene that encodes β-glucosidase, and increasing the expression of the gene in the plant. Of particular interest are β-glucosidases capable of cleaving hydroxamic acid glucosides, more particularly, maize β-glucosidase.

β-glucosidases catalyze the hydrolysis of glycosidic linkages in a variety of aryl and alkyl β-glucosides such as the hydroxamic acid glucoside (DIMBOA-glc) in maize. Maize β-glucosidase is encoded by two closely related β-glucosidase isozymes designated Glu1 and Glu2. The Glu1 gene maps to chromosome 10. The maize Glu1 gene has been cloned and sequenced. See, Esen et al. (1992) *Plant Physiol.* 98: 174–182; Brzobohaty et al. (1993) *Science* 262:1051–1054; herein incorporated by reference. However, it is recognized that Glu2 or other β-glucosidases can be utilized. β-glucosidases use a double displacement to hydrolyze their substrates with a covalently linked enzyme-substrate intermediate. Hydrolysis occurs at the active center with two acidic residues (Asp/Glu) participating. Esen, β-*glucosidases: Biochemistry and Molecular Biology* (Asim Esen, editor) 1993 ACS Symposium Series pg. 1–14.

The invention is drawn to compositions and methods for enhancing disease resistance in a plant. By "disease resistance" is intended that the plants avoid the disease symptoms that are the outcome of plant-pathogen interactions and thereby display a decreased susceptibility to plant pathogens. That is, pathogens are prevented from causing plant diseases and the associated disease symptoms, or alternatively, the disease symptoms caused by the pathogen is minimized or lessened. The methods of the invention can be utilized to protect plants from disease, particularly those diseases that are caused by plant pathogens. Accordingly, the compositions and methods are useful in protecting plants from a variety of pathogenic organisms or pests including, but not limited to, bacteria, fungi, viruses, viroids, nematodes, insects, and the like.

The gene encoding β-glucosidase, for example Glu1 and Glu2, that will be used for the purposes of this invention may come from any source. The expression of the β-glucosidase gene enhances resistance to plant diseases. While the invention is not bound by any particular mechanism, generally the enzyme is capable of cleaving hydroxyamic acid glucosides as well as glucosyl conjugates of other compounds produced in the hydroxyamic acid biosynthetic pathway, for example the pathway governed by the Bx1 gene. (See Frey et al. (1995) *Mol. Gen. Genet.* 246:100–109; and U.S. patent application Ser. No. 09/034,298.) The enzyme may additionally function by cleaving other conjugates as long as the action leads to disease resistance. For example, β-glucosidase can cleave salicylic acid glucosyl (Chen et al. (1995) *Proc. Natl. Acac. Sci. USA* 92:4134–4137); and phytohormone conjugates (Brzobohaty et al. (1993) *Science* 262:1051–1054. Additionally, β-glucosidase can release other substances that may affect pathogens, including fungi (Ito T, and Kumazawa K (1995) *Biosci. Biotech. Biochem.* 59:1944–1945); and can release volatile compounds that can affect pathogens and insects (Hopke et al. (1994) *FEBS Letters* 352:146–150).

Genes that encode β-glucosidase are ubiquitous in nature and may be isolated from both prokaryotic and eukaryotic organisms. Examples of prokaryotes and eukaryotes that have genes encoding β-glucosidase that have been cloned and sequenced include but are not limited to Agrobacterium sp., Wakarchuk et al. (1988) *J. Bacteriol.* 170:301–307; *Bacillus subtilis*, Ogasawara et al. (1995) *Microbiology* 141:257–259; *Candida pelliculosa*, Kohchi et al. (1985) *Nucleic Acids Res.* 13:6273–6282; *Candida wickershaamii*, Skory et al. (1995) *Appl. Environ. Microbiol.* 61:518–525; *S. cerevisiae*, San Segundo et al. (1993) *J. Biol. Chem.* 175:3823–3837; *Chizophyllum commune*, Moranelli et al. (1986) *Biochem. Int.* 12:905–912; *E. coli* (ascB gene), Hall et al. (1992) *Mol. Biol. Evol.* 9:688–706; *Cellvibrio geilvus*, Singh, A. (1995) *Biochem J.* 305:715–719; *Nicotiana tabacum*, Sperisen et al. (1991) *Proc. Natl. Acad Sci. U.S.A.* 88: 1820–1824; *Zea mays* (Glu1 gene), Esen et al. (1992) *Plant Physiol.* 98:174–182; *Zea mays* (Glu2 gene), Bandaranayake et al. (1996) *Plant Physiol.* 110:1048; *Sulfolobus solfataricus*, Little et al. (1989) *Nucleic Acids Res.* 17:7980–7980; *Escherichia coli*, Le Coq et al. (1995) *J. Bacteriol.* 177:1527–1535; *Bacillus polymyxa*, Gonzalez-Candelas et al. (1990) *Gene* 95:31–38; *Thermotoga maritima*, Liebl et al. (1994) *Mol. Gen. Genet.* 242:111–115; *Trifolium repens*, Oxtoby et al. (1991) *Plant Mol. Biol.* 17:209–219; *Arabidopsis thaliana*, Malboobi et al. (1996) *Plant Physiol.* 112:1399; *Pinus contorta* U.S. Pat. No. 5,973,228; *Hordeum vulgare*, Xu et al. (1992) *Gene* 120:157–165; *Brassica nigra*, Malboobi et al (1995) *Plant Mol. Biol.* 28:859–870. Such disclosures are herein incorporated by reference.

The methods of the invention work by increasing expression of the β-glucosidase. By "increasing the expression" is intended that the β-glucosidase gene is transcribed and translated at such levels that the amount of protein (β-glucosidase) produced in the transformed plant exceeds the amount of protein produced in the untransformed plant. Likewise, it encompasses expression in tissues where no, or little, β-glucosidase is found in the native tissue, such as for example mature leaves. It is also intended that the increased expression of said gene in the plant system is sufficient to generate an increase in the activity of the protein. Generally, the activity of the protein in the transformed plant or tissue is at least about 10 to about 25 to about 50% higher than that of the untransformed plant or tissue, preferably at least about 50 to about 100% higher, and more preferably at least about 100 to about 200% to about 400% and higher.

To modify action in the plant or to enhance disease resistance, the β-glucosidase proteins of the invention may be altered in various ways including amino acid substitutions, deletions, truncations and insertions. Such variants and fragments of the proteins are encompassed within the scope of the invention. By "fragment" is intended a portion of the nucleotide sequence or a portion of the amino acid sequence and hence protein encoded thereby. Fragments of a nucleotide sequence may encode protein fragments that retain the biological activity of the native protein and hence enhance disease resistance. Alternatively, fragments of a nucleotide sequence that are useful as hybridization probes generally do not encode fragment proteins retaining biological activity. Thus, fragments of a nucleotide sequence may range from at least about 20 nucleotides, about 50 nucleotides, about 100 nucleotides, and up to the full-length nucleotide sequence encoding the proteins of the invention.

A fragment of a β-glucosidase nucleotide sequence that encodes a biologically active portion of a β-glucosidase protein of the invention will encode at least 15, 25, 30, 50, 100, 150, 200, 250, 300, 400, 500, 550 contiguous amino acids, or up to the total number of amino acids present in a full-length β-glucosidase protein. Fragments of a β-glucosidase nucleotide sequence that are useful as hybridization probes or PCR primers generally need not encode a biologically active portion of a β-glucosidase protein.

Thus, a fragment of a β-glucosidase nucleotide sequence may encode a biologically active portion of a β-glucosidase protein, or it may be a fragment that can be used as a hybridization probe or PCR primer using methods disclosed below. A biologically active portion of a β-glucosidase protein can be prepared by isolating a portion of one of the β-glucosidase nucleotide sequences of the invention, expressing the encoded portion of the β-glucosidase protein (e.g., by recombinant expression in vitro), and assessing the activity of the encoded portion of the β-glucosidase. Nucleic acid molecules that are fragments of a β-glucosidase nucleotide sequence comprise at least 16, 20, 50, 75, 100, 150, 200, 250, 300, 350, 400, 450, 500, 550, 600, 650, 700, 800, 900, 1,000, 1,100, 1,200, 1,300, 1,400, 1,500, 1,600, 1,700, 1,800, 1,900 nucleotides, or up to the number of nucleotides present in a full-length β-glucosidase nucleotide sequence disclosed herein.

By "variants" is intended substantially similar sequences. For nucleotide sequences, conservative variants include those sequences that, because of the degeneracy of the genetic code, encode the amino acid sequence of one of the β-glucosidase polypeptides of the invention. Naturally occurring allelic variants such as these can be identified with the use of well-known molecular biology techniques, as, for example, with polymerase chain reaction (PCR) and hybridization techniques as outlined below. Variant nucleotide sequences also include synthetically derived nucleotide sequences, such as those generated, for example, by using site-directed mutagenesis but which still encode a β-glucosidase protein of the invention. Generally, variants of a particular nucleotide sequence of the invention will have at least 60%, 70%, generally at least 75%, 80%, 85%, preferably about 90% to 95% or more, and more preferably about 98% or more sequence identity to that particular nucleotide sequence as determined by sequence alignment programs described elsewhere herein using default parameters.

By "variant" protein is intended a protein derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Variant proteins encompassed by the present invention are biologically active, that is they continue to possess the desired biological activity of the native protein, that is, enhance disease resistance as described herein. Such variants may result from, for example, genetic polymorphism or from human manipulation. Biologically active variants of a native β-glucosidase protein of the invention will have at least 60%, 70%, generally at least 75%, 80%, 85%, preferably about 90% to 95% or more, and more preferably about 98% or more sequence identity to the amino acid sequence for the native protein as determined by sequence alignment programs described elsewhere herein using default parameters. A biologically active variant of a protein of the invention may differ from that protein by as few as 1–15 amino acid residues, as few as 1–10, such as 6–10, as few as 5, as few as 4, 3, 2, or even 1 amino acid residue.

The proteins of the invention may be altered in various ways including amino acid substitutions, deletions, truncations, and insertions. Methods for such manipulations are generally known in the art. For example, amino acid sequence variants of the β-glucosidase proteins can be prepared by mutations in the DNA. Methods for mutagenesis and nucleotide sequence alterations are well known in the art. See, for example, Kunkel (1985) *Proc. Natl. Acad Sci. USA* 82:488–492; Kunkel et al. (1987) *Methods in Enzymol.* 154:367–382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be preferred.

Thus, the genes and nucleotide sequences of the invention include both the naturally occurring sequences as well as mutant forms. Likewise, the proteins of the invention encompass both naturally occurring proteins as well as variations and modified forms thereof. Such variants will continue to possess the desired β-glucosidase activity. Obviously, the mutations that will be made in the DNA encoding the variant must not place the sequence out of reading frame and preferably will not create complementary regions that could produce secondary mRNA structure. See, EP Patent Application Publication No. 75,444.

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays. That is, the activity can be evaluated by an altered disease resistance in plants or by assaying for β-glucosidase activity. Such assays are known in the art. See, for example, Babcock et al. (1994) *Plant Science* 101: 31–39, herein incorporated by reference.

Variant nucleotide sequences and proteins also encompass sequences and proteins derived from a mutagenic and recombinogenic procedure such as DNA shuffling. With such a procedure, one or more different β-glucosidase coding sequences can be manipulated to create a new β-glucosidase possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between two β-glucosidase genes to obtain a new gene coding for a protein with an improved property of interest, such as an increased $K_m$ in the case of an enzyme. Strategies for such DNA shuffling are known in the art. See, for example, Stemmer (1994) *Proc. Natl. Acad. Sci. USA* 91:10747–10751; Stemmer (1994) *Nature* 370:389–391; Crameri et al. (1997) *Nature Biotech*. 15:436–438; Moore et al. (1997) *J. Mol. Biol.* 272:336–347; Zhang et al. (1997) *Proc. Natl. Acad. Sci. USA* 94:4504–4509; Crameri et al. (1998) *Nature* 391:288–291; and U.S. Pat. Nos. 5,605,793 and 5,837,458.

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent sequence identity between any two sequences can be accomplished using a mathematical algorithm. Preferred, non-limiting examples of such mathematical algorithms are the algorithm of Myers and Miller (1988) *CABIOS* 4:11–17; the local homology algorithm of Smith et al. (1981) *Adv. Appl. Math.* 2:482; the homology alignment algorithm of Needleman and Wunsch (1970) *J. Mol. Biol.* 48:443–453; the search-for-similarity-method of Pearson and Lipman (1988) *Proc. Natl. Acad Sci*. 85:2444–2448; the algorithm of Karlin and Altschul (1990) *Proc. Natl. Acad Sci. USA* 872264, modified as in Karlin and Altschul (1993) *Proc. Natl. Acad. Sci. USA* 90:5873–5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al. (1988) *Gene* 73:237–244 (1988); Higgins et al. (1989) *CABIOS* 5:151–153; Corpet et al. (1988) *Nucleic Acids Res*. 16:10881–90; Huang et al. (1992) *CABIOS* 8:155–65; and Pearson et al. (1994) *Meth. Mol. Biol*. 24:307–331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul et al (1990) *J. Mol. Biol*. 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the invention. BLAST protein searches can be performed with the BLASTX program, score=50, wordlength=3, to obtain amino acid sequences homologous to a protein or polypeptide of the invention. To obtain gapped alignments for comparison purposes, Gapped BLAST (in BLAST 2.0) can be utilized as described in Altschul et al. (1997) *Nucleic Acids Res*. 25:3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for proteins) can be used. See http://www.ncbi.nlm.nih.gov. Alignment may also be performed manually by inspection.

For purposes of the present invention, comparison of nucleotide or protein sequences for determination of percent sequence identity to the β-glucosidase sequences disclosed herein is preferably made using the Clustal W program Version 1.7 or later. with its default parameters or any equivalent program. By "equivalent program" is intended any sequence comparison program that, for any two sequences in question, generates an alignment having identical nucleotide or amino acid residue matches and an identical percent sequence identity when compared to the corresponding alignment generated by the preferred program.

(c) As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide comprises a sequence that has at least 70% sequence identity, preferably at least 80%, more preferably at least 90%, and most preferably at least 95%, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 60%, more preferably at least 70%, 80%, 90%, and most preferably at least 95%.

Another indication that nucleotide sequences are substantially identical is if two molecules hybridize to each other under stringent conditions. Generally, stringent conditions are selected to be about 5° C. lower than the thermal melting point ($T_m$) for the specific sequence at a defined ionic strength and pH. However, stringent conditions encompass temperatures in the range of about 1° C. to about 20° C., depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(e)(ii) The term "substantial identity" in the context of a peptide indicates that a peptide comprises a sequence with at least 70% sequence identity to a reference sequence, preferably 80%, more preferably 85%, most preferably at least 90% or 95% sequence identity to the reference sequence over a specified comparison window. Preferably, optimal alignment is conducted using the homology alignment algorithm of Needleman and Wunsch (1970) *J. Mol. Biol*. 48:443–453. An indication that two peptide sequences are substantially identical is that one peptide is immunologically all reactive with antibodies raised against the second peptide. Thus, a peptide is substantially identical to a second peptide, for example, where the two peptides differ only by a conservative substitution. Peptides that are "substantially similar" share sequences as noted above except that residue positions that are not identical may differ by conservative amino acid changes.

In a PCR approach, oligonucleotide primers can be designed for use in PCR reactions to amplify corresponding DNA sequences from cDNA or genomic DNA extracted from any organism of interest. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}$p, or any other detectable marker. Thus, for example, probes for hybridization can be made by labeling synthetic oligonucleotides based on the β-glucosidase sequences of the invention. Methods for preparation of probes for hybridization and for construction of cDNA and genomic libraries are generally known in the art and are disclosed in Sambrook et al. (1989) *Molecular Cloning: A Laboratory Manual* (2d ed., Cold Spring Harbor Laboratory Press, Plainview, N.Y.).

For example, the entire β-glucosidase sequence, or one or more portions thereof, may be used as a probe capable of specifically hybridizing to corresponding β-glucosidase sequences and messenger RNAs. To achieve specific hybridization under a variety of conditions, such probes include sequences that are unique among β-glucosidase sequences and are preferably at least about 10 nucleotides in length, and most preferably at least about 20 nucleotides in length. Such probes may be used to amplify corresponding ,B-glucosidase sequences from a chosen organism by PCR. This technique may be used to isolate additional coding sequences from a desired organism or as a diagnostic assay to determine the presence of coding sequences in a an organism. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Plainview, N.Y.).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267–284. $T_m$=81.5° C.+16.6 (log M)+0.41 (%GC)−0.61 (% form)−500/L; where M is the molarity of monovalent cations, %GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology-Hybridization with Nucleic Acid Probes*, Part I, Chapter 2 (Elsevier, N.Y.); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Plainview, N.Y.).

Thus, isolated sequences that encode for a β-glucosidase protein and which hybridize under stringent conditions to the β-glucosidase sequences, or to fragments thereof, are encompassed by the present invention. Such sequences will be at least about 40% to 50%, 60% to 70% homologous, and even about 75%, 80%, 85%, 90%, 95% to 98% homologous or more with the disclosed sequences. That is, the sequence identity of sequences may range, sharing at least 40% to 50%, about 60% to 70%, and even about 75%, 80%, 85%, 90%, 95% to 98% or more sequence identity.

It is recognized that the plant cell can be transformed with a nucleotide sequence encoding β-glucosidase or a nucleotide sequence encoding a portion of β-glucosidase. In this manner, the level of expression of β-glucosidase in the plant cell can be increased. Levels of expression of the β-glucosidase can be regulated by the promoter utilized to express the gene. Such promoter may include, for example, constitutive, tissue-preferred, or any other promoter that drive expression in plants. Of particular interest are promoters that drive expression in leaves and roots, but not seeds. Promote can also be chosen to control temporal specificity, i.e., promoters that drive expression in mature plants or later in development.

Such constitutive promoters include, for example, 35S promoter, Meyer et al. (1997) *J. Gen. Virol.* 78:3147–3151; biotin carboxylase, Bas et al. (1997) *Plant Mol. Biol.* 35:539–550; oxidase, Lasserre et al. (1997) *Mol. Gen. Genet* 256:211–222; cab, Shiina et al. (1997) *Plant Physiol.* 115:477–483; phospholipase, Xu et al. (1997) *Plant Physiol.* 115:387–395; farnesyltransferase, Zhou et al. (1997) *Plant J.* 12:921–930; plastocyanin, Helliwell et al. (1997) *Plant J.* 12:499–506; CVMV promoter, Verdaquer et al. (1996) *Plant Mol. Biol.* 31:1129–1139; actin, An et al. (1996) *Plant J.* 10: 107–121; heat shock, Prandl et al. (1996) *Plant Mol. Biol.* 31:157–162; ubiquitin, thionin, 35S, Holtorf et al. (1995) *Plant Mol. Biol.* 29:637–646; Callis et al. (1990) *J. Biol. Chem.* 265:12486–12493; histone, Atanossova et al. (1992) *Plant J.* 2:291–300; rol C, Fladung et al. (1993) *Plant Mol. Biol.* 23:749–757; histone, Brignon et al. (1993) *Plant J.* 4:445–457; Lepetit et al. (1992) Mol. Gen. Genet. 231:276–285; rice actin (McElroy et al. (1990) *Plant Cell* 2:163–171); ubiquitin (Christensen et al. (1989) *Plant Mol. Biol.* 12:619–632 and Christensen et al. (1992) *Plant Mol. Biol.* 18:675–689); pEMU (Last et al. (1991) *Theor. Appl. Genet.* 81:581–588); MAS (Velten et al. (1984) *EMBO J.* 3:2723–2730); ALS promoter (U.S. Pat. No. 5,659,026), and the like. Additional constitutive promoters include, for example, those disclosed in U.S. Pat. Nos. 5,608,149; 5,608,144; 5,604,121; 5,569,597; 5,466,785; 5,399,680; 5,268,463; 5,608,142, herein incorporated by reference.

Generally, it will be beneficial to express the gene from an inducible promoter, particularly from a pathogen-inducible promoter. Such promoters include those from pathogenesis-related proteins (PR proteins), which are induced following infection by a pathogen; e.g., PR proteins, SAR proteins, beta-1,3-glucanase, chitinase, etc. See, for example, Redolfi et al. (1983) *Neth. J. Plant Pathol.* 89:245–254; Uknes et al. (1992) *Plant Cell* 4:645–656; and Van Loon (1985) *Plant Mol. Virol.* 4:111–116. See also the copending application entitled "Inducible Maize Promoters," U.S. application Ser. No. 09/257,583, filed Feb. 25, 1999, herein incorporated by reference.

Of interest are promoters that are expressed locally at or near the site of pathogen infection. See, for example, Marineau et al. (1987) *Plant Mol. Biol.* 9:335–342; Matton et al. (1989) *Molecular Plant-Microbe Interactions* 2:325–331; Somsisch et al. (1986) *Proc. Natl. Acad Sci. USA* 83:2427–2430; Somsisch et al. (1988) *Mol. Gen. Genet.* 2:93–98; and Yang (1996) *Proc. Natl. Acad Sci. USA* 93:14972–14977. See also, Chen et al. (1996) *Plant J.* 10:955–966; Zhang et al. (1994) *Proc. Natl. Acad. Sci. USA* 91:2507–2511; Warner et al. (1993) *Plant J.* 3:191–201; Siebertz et al. (1989) *Plant Cell* 1:961–968; U.S. Pat. No. 5,750,386 (nematode-inducible); and the references cited therein. Of particular interest is the inducible promoter for the maize PRms gene, whose expression is induced by the pathogen *Fusarium moniliforme* (see, for example, Cordero et al. (1992) *Physiol. Mol. Plant Path.* 41:189–200).

Tissue-preferred promoters can be utilized to target enhanced β-glucosidase expression within a particular plant tissue. Tissue-preferred promoters include Yamamoto et al. (1997) *Plant J.* 12(2)255–265; Kawamata et al. (1997) *Plant Cell Physiol.* 38(7):792–803; Hansen et al. (1997) *Mol. Gen Genet.* 254(3):337–343; Russell et al. (1997) *Transgenic Res.* 6(2):157–168; Rinehart et al. (1996) *Plant Physiol.* 112(3):1331–1341; Van Camp et al. (1996) *Plant Physiol.* 112(2):525–535; Canevascini et al. (1996) *Plant Physiol.* 112(2):513–524; Yamamoto et al. (1994) *Plant Cell Physiol.* 35(5):773–778; Lam (1994) *Results Probl. Cell Differ.* 20:181–196; Orozco et al. (1993) *Plant Mol Biol.* 23(6): 1129–1138; Matsuoka et al. (1993) *Proc Natl. Acad. Sci. USA* 90(20):9586–9590; and Guevara-Garcia et al. (1993) *Plant J.* 4(3):495–505. Such promoters can be modified, if necessary, for weak expression.

Leaf-specific promoters are known in the art. See, for example, Yamamoto et al. (1997) *Plant J.* 12(2):255–265; Kwon et al. (1994) *Plant Physiol.* 105:357–67; Yamamoto et al. (1994) *Plant Cell Physiol.* 35(5):773–778; Gotor et al. (1993) *Plant J.* 3:509–18; Orozco et al. (1993) *Plant Mol. Biol.* 23(6): 1129–1138; and Matsuoka et al. (1993) *Proc. Natl. Acad Sci. USA* 90(20):9586–9590.

Root-specific promoters are known and can be selected from the many available from the literature or isolated de novo from various compatible species. See, for example, Hire et al. (1992) *Plant Mol. Biol.* 20(2): 207–218 (soybean root-specific glutamine synthetase gene); Keller and Baumgartner (1991) *Plant Cell* 3(10):1051–1061 (root-specific control element in the GRP 1.8 gene of French bean); Sanger et al. (1990) *Plant Mol. Biol.* 14(3):433–443 (root-specific promoter of the mannopine synthase (MAS) gene of *Agrobacterium tumefaciens*); and Miao et al. (1991) *Plant Cell* 3(1):11–22 (full-length cDNA clone encoding cytosolic glutamine synthetase (GS), which is expressed in roots and root nodules of soybean). See also Bogusz et al. (1990) *Plant Cell* 2(7):633–641, where two root-specific promoters isolated from hemoglobin genes from the nitrogen-fixing non-legume *Parasponia andersonii* and the related non-nitrogen-fixing nonlegume *Trema tomentosa* are described. The promoters of these genes were linked to a β-glucuronidase reporter gene and introduced into both the nonlegume *Nicotiana tabacum* and the legume *Lotus corniculatus*, and in both instances root-specific promoter activity was preserved. Leach and Aoyagi (1991) describe their analysis of the promoters of the highly expressed rolC and rolD root-inducing genes of *Agrobacterium rhizogenes* (see *Plant Science* (Limerick) 79(1):69–76). They concluded that enhancer and tissue-preferred DNA determinants are dissociated in those promoters. Teeri et al. (1989) used gene fusion to lacZ to show that the Agrobacterium T-DNA gene encoding octopine synthase is especially active in the epidermis of the root tip and that the TR2' gene is root specific in the intact plant and stimulated by wounding in leaf tissue, an especially desirable combination of characteristics for use with an insecticidal or larvicidal gene (see *EMBO J.* 8(2)

:343–350). The TR1' gene, fused to nptII (neomycin phosphotransferase II) showed similar characteristics. Additional root-preferred promoters include the VfENOD-GRP3 gene promoter (Kuster et al. (1995) *Plant Mol. Biol.* 29(4) :759–772); and rolB promoter (Capana et al. (1994) *Plant Mol. Biol.* 25(4):681–691. See also U.S. Pat. Nos. 5,837, 876; 5,750,386; 5,633,363; 5,459,252; 5,401,836; 5,110, 732; and 5,023,179.

Of particular interest are strong promoters leading to an increased expression of the β-glucosidase. By "strong promoter" is intended any promoter whether constitutive, inducible or tissue specific which is utilized to achieve high levels of expression of genes introduced into higher plants. Strong promoters are available and are known to those of skill in the art. Strong promoters are often characterized by the efficiency and strength of RNA polymerase binding, which is a function of the DNA sequence characteristics of promoter elements such as the TATA box motif as well as other cis elements and trans acting factors which aid in transcriptional complex assembly. In this manner, a strong constitutive promoter causing an elevated expression of β-glucosidase may be utilized. In terms of number of transcripts per total mRNA, a strong constitutive promoter would produce about 1/10 transcripts to about 1/100 transcripts to about 1/1,000 transcripts.

The gene encoding the β-glucosidase used in this invention can be transformed into a suitable host either alone or in conjunction with other genes which may aid in pathogen resistance. Genes that may be useful in this capacity include, but are not limited to, those that encode early DIMBOA biosynthetic pathway enzymes. This approach prevents the hydroxamic acid glucoside substrate such as DIMBOA-glc for β-glucosidase from becoming limited as the plant matures. Hydroxamic acids play a major role in the defense of the plant against certain pests. Genes that might be used include the CYP7IC (Bx) genes of the DIMBOA biosynthetic pathway, examples of which include Bx2, Bx3, Bx4, and Bx5. See, Frey et al. (1995) *Mol. Gen. Genet.* 246: 100–109 and copending U.S. application Ser. No. 09/034, 298, both of which are herein incorporated by reference.

The β-glucosidase nucleotides, as well as other pathogen resistance enhancing genes, can be introduced into any plant.

The present invention may be used for transformation of any plant species, including, but not limited to, corn (*Zea mays*), Brassica sp. (e.g., *B. napus, B. rapa, B. juncea*), particularly those Brassica species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Cofea spp.*), coconut (*Cocos nucifera*), pineapple (*Ananas comosus*), citrus trees (*Citrus spp.*), cocoa (*Theobroma cacao*), tea (*Camellia sinensis*), banana (*Musa spp.*), avocado (*Persea americana*), fig (*Ficus casica*), guava (*Psiaium guajava*), mango (*Mangifera indica*), olive (*Olea europaea*), papaya (*Carica papaya*), cashew (*Anacardium occidentale*), macademia (*Macadamia integrifolia*), almond (*Prunus amygdalus*), sugar beets (*Beta vulgaris*), sugarcane (*Saccharum spp.*), oats, barley, vegetables, ornamentals, and conifers.

The genes or nucleotide sequences to be introduced will be used in expression cassettes for expression in any plant of interest. Such expression cassettes will comprise a transcriptional initiation region linked to the gene encoding the β-glucosidase nucleotide of interest. Such an expression cassette is provided with a plurality of restriction sites for insertion of the gene of interest to be under the transcriptional regulation of the regulatory regions. The expression cassette may additionally contain selectable marker genes.

The transcriptional initiation region, the promoter, may be native or analogous or foreign or heterologous to the plant host. Additionally, the promoter may be the natural sequence or alternatively a synthetic sequence. By foreign is intended that the transcriptional initiation region is not found in the native plant into which the transcriptional initiation region is introduced. As used herein a chimeric gene comprises a coding sequence operably linked to a transcription initiation region that is heterologous to the coding sequence.

While it may be preferable to express the sequences using heterologous promoters, the native promoter sequences may be used. Such constructs would change expression levels of β-glucosidase in the plant or plant cell. Thus, the phenotype of the plant or plant cell is altered.

The transcriptional cassette will include in the 5'-3' direction of transcription, a transcriptional and translational initiation region, a DNA sequence of interest, and a transcriptional and translational termination region functional in plants. The termination region may be native with the transcriptional initiation region, may be native with the DNA sequence of interest, or may be derived from another source. Convenient termination regions are available from the Ti-plasmid of *A. tumefaciens*, such as the octopine synthase and nopaline synthase termination regions. See also, Guerineau et al., (1991) *Mol. Gen. Genet.* 262:141–144; Proudfoot et al. (1991) *Cell* 64:671–674; Sanfacon et al. (1991) *Genes Dev.* 5:141–149; Mogen et al. (1990) *Plant Cell* 2:1261–1272; Munroe et al. (1990) *Gene* 91:151–158; Ballas et al. (1989) *Nucleic Acids Res.* 17:7891–7903; Joshi et al. (1987) *Nucleic Acid Res.* 15:9627–9639.

Where appropriate, the gene(s) may be optimized for increased expression in the transformed plant. That is, the genes can be synthesized using plant preferred codons for improved expression. Methods are available in the art for synthesizing plant preferred genes. See, for example, U.S. Pat. Nos. 5,380,831, 5,436, 391, and Murray et al. (1989) *Nucleic Acids Res.* 17:477–498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences which may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences in the expression cassette construct. Such leader sequences can act to enhance translation. Translation leaders are known in the art and include: picornavirus leaders, for example, EMCV leader (Encephalomyocarditis 5' noncoding region) (Elroy-Stein et al. (1989) *PNAS USA* 86:6126–6130); potyvirus leaders, for example, TEV leader (Tobacco Etch Virus) (Allison et al. (1986); MDMV leader (Maize Dwarf Mosaic Virus); *Virology* 154:9-20), and human immunoglobulin heavy-chain binding protein (BiP), (Macejak et al. (1991) *Nature* 353:90–94; untranslated leader from the coat protein mRNA of alfalfa mosaic virus (AMV RNA 4), (Jobling et al. (1987) *Nature* 325:622–625; tobacco mosaic virus leader (TMV), (Gallie et al. (1989) *Mole. Biol. of RNA*, pp.237–256; and maize chlorotic mottle virus leader (MCMV) (Lommel et al. (1991) *Virology* 81:382–385). See also, Della-Cioppa et al. (1987) *Plant Physiology*, 84:965–968. Other methods known to enhance translation can also be utilized, for example, introns, and the like.

In preparing the expression cassette, the various DNA fragments may be manipulated, so as to provide for the DNA sequences in the proper orientation and, as appropriate, in the proper reading frame. Towards this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g. transitions and transversions, may be involved.

The genes of the present invention can be used to transform any plant. In this manner, genetically modified plants, plant cells, plant tissue, seed, and the like can be obtained. Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway et al. (1986) *Biotechniques* 4:320–334), electroporation (Riggs et al. (1986) *Proc. Natl. Acad. Sci. USA* 83:5602–5606, Agrobacterium-mediated transformation (Townsend et al., U.S. Pat No. 5,563,055), direct gene transfer (Paszkowski et al. (1984) *EMBO J.* 3:2717–2722), and ballistic particle acceleration (see, for example, Sanford et al., U.S. Pat. No. 4,945,050; Tomes et al., U.S. Pat. No. 5,879,918; Tomes et al., U.S. Pat. No. 5,886,244; Bidney et al., U.S. Pat. No. 5,932,782; Tomes et al. (1995) "Direct DNA Transfer into Intact Plant Cells via Microprojectile Bombardment," in *Plant Cell, Tissue, and Organ Culture: Fundamental Methods*, ed. Gamborg and Phillips (Springer-Verlag, Berlin); and McCabe et al. (1988) *Biotechnology* 6:923–926). Also see Weissinger et al. (1988) *Ann. Rev. Genet.* 22:421–477; Sanford et al. (1987) *Particulate Science and Technology* 5:27–37 (onion); Christou et al. (1988) *Plant Physiol.* 87:671–674 (soybean); McCabe et al. (1988) *Bio/Technology* 6:923–926 (soybean); Finer and McMullen (1991) *In Vitro Cell Dev. Biol.* 27P: 175–182 (soybean); Singh et al. (1998) *Theor. Appl. Genet.* 96:319–324 (soybean); Datta et al. (1990) *Biotechnology* 8:736–740 (rice); Klein et al. (1988) *Proc. Natl. Acad Sci. USA* 85:4305–4309 (maize); Klein et al. (1988) *Biotechnology* 6:559–563 (maize); Tomes, U.S. Pat. No. 5,240,855; Buising et al., U.S. Pat. Nos. 5,322,783 and 5,324,646; Tomes et al. (1995) "Direct DNA Transfer into Intact Plant Cells via Microprojectile Bombardment," in *Plant Cell, Tissue, and Organ Culture: Fundamental Methods*, ed. Gamborg (Springer-Verlag, Berlin) (maize); Klein et al. (1988) *Plant Physiol.* 91:440–444 (maize); Fromm et al. (1990) *Biotechnology* 8:833–839 (maize); Hooykaas-Van Slogteren et al. (1984) *Nature (London)* 311:763–764; Bowen et al., U.S. Pat. No 5,136,369 (cereals); Bytebier et al (1987) *Proc. Natl. Acad Sci. USA* 84:5345–5349 (Liliaceae); De Wet et al. (1985) in *The Experimental Manipulation of Ovule Tissues*, ed. Chapman et al. (Longman, New York), pp. 197–209 (pollen); Kaeppler et al. (1990) *Plant Cell Reports* 9:415–418 and Kaeppler et al. (1992) *Theor. Appl. Genet.* 84:560–566 (whisker-mediated transformation); D'Halluin et al. (1992) *Plant Cell* 4:1495–1505 (electroporation); Li et al. (1993) *Plant Cell Reports* 12:250–255 and Christou and Ford (1995) *Annals of Botany* 75:407–413 (rice); Osjoda et al. (1996) *Nature Biotechnology* 14:745–750 (maize via *Agrobacterium tumefaciens*); all of which are herein incorporated by reference.

The cells which have been transformed may be grown into plants in accordance with conventional ways. See, for example, McCormick et al. (1986) *Plant Cell Reports* 5:81–84. These plants may then be grown, and either pollinated with the same transformed strain or different strains, and the resulting hybrid having the desired phenotypic characteristic identified. Two or more generations may be grown to ensure that the subject phenotypic characteristic is stably maintained and inherited and then seeds harvested to ensure the desired phenotype or other property has been achieved.

As noted earlier, the methods of the invention can be utilized to protect plants from disease, particularly those diseases that are caused by plant pathogens. For purposes of the present invention, pathogens include but are not limited to insects, fungi, bacteria, nematodes, viruses or viroids, and the like.

Viruses include any plant virus, for example, tobacco or cucumber mosaic virus, ringspot virus, necrosis virus, maize dwarf mosaic virus, etc. Specific fungal and viral pathogens for the major crops include: Soybeans: *Phytophthora megasperma* fsp. *glycinea, Macrophomina phaseolina, Rhizoctonia solani, Sclerotinia sclerotiorum, Fusarium oxysporum, Diaporthe phaseolorum* var. *sojae* (*Phomopsis sojae*), *Diaporthe phaseolorum* var. *caulivora, Sclerotium rolfsii, Cercospora kikuchii, Cercospora sojina, Peronospora manshurica, Colletotrichum dematium* (*Colletotichum truncatum*), *Corynespora casssticola, Septoria glycines, Phyllosticta sojicola, Alternaria alternata, Pseudomonas syringae* p.v. *glycinea, Xanthomonas campestris* p.v. *phaseoli, Microsphaera diffusa, Fusarium semitectum, Phialophora gregata*, Soybean mosaic virus, *Glomerella glycines*, Tobacco Ring spot virus, Tobacco Streak virus, *Phakopsora pachyrhizi, Pythium aphanidermatum, Pythium ultimum, Pythium debaryanum*, Tomato spotted wilt virus, *Heterodera glycines Fusarium solani*; Canola: *Albugo candida, Alternaria brassicae, Leptosphaeria maculans, Rhizoctonia solani, Sclerotinia sclerotiorum, Mycosphaerella brassiccola, Pythium ultimum, Peronosporaparasitica, Fusarium roseum, Alternaria alternata*; Alfalfa: *Clavibater michiganese* subsp. *insidiosum, Pythium ultimum, Pythium irregulare, Pythium splendens, Pythium debaryanum, Pythium aphanidermatum, Phytophthora megasperma, Peronospora trifoliorum, Phoma medicaginis* var. *medicaginis, Cercospora medicaginis, Pseudopeziza medicaginis, Leptotrochila medicaginis, Fusarium, Xanthomonas campestris* p.v. *alfalfae, Aphanomyces euteiches, Stemphylium herbarum, Stemphylium alfalfae*; Wheat: *Pseudomonas syringae* p.v. *atrofaciens, Urocystis agropyri, Xanthomonas campestris* p.v. *translucens, Pseudomonas syringae* p.v. *syringae, Alternaria alternata, Cladosporium herbarum, Fusarium graminearum, Fusarium avenaceum, Fusarium culmorum, Ustilago tritici, Ascochyta tritici, Cephalosporium gramineum, Collotetrichum graminicola, Erysiphe graminis* f.sp. *tritici, Puccinia graminis* f.sp. *tritici, Puccinia recon-* dita f.sp. *tritici, Puccinia striiformis, Pyrenophora tritici-repentis, Septoria nodorum, Septoria tritici, Septoria avenae, Pseudocercosporella herpotrichoides, Rhizoctonia solani, Rhizoctonia cerealis, Gaeumannomyces graminis* var. *tritici, Pythium aphanidermatum, Pythium arrhenomanes, Pythium ultimum, Bipolaris sorokiniana,* Barley Yellow Dwarf Virus, Brome Mosaic Virus, Soil Borne Wheat Mosaic Virus, Wheat Streak Mosaic Virus, Wheat Spindle Streak Virus, American Wheat Striate Virus, *Claviceps purpurea, Tilletia tritici, Tilletia laevis, Ustilago tritici, Tilletia indica, Rhizoctonia solani, Pythium arrhenomannes, Pythium gramicola, Pythium aphanidermatum,* High Plains Virus, European wheat striate virus; Sunflower: *Plasmophora halstedii, Sclerotinia sclerotiorum,* Aster Yellows, *Septoria helianthi, Phomopsis helianthi, Alternaria helianthi, Alternaria zinniae, Botrytis cinerea, Phoma macdonaldii, Macrophominaphaseolina, Erysiphe cichoracearum, Rhizopus oryzae, Rhizopus arrhizus, Rhizopus stolonifer, Puccinia helianthi, Verticillium dahliae, Erwinia carotovorum* pv. *carotovora, Cephalosporium acremonium, Phytophthora cryptogea, Albugo tragopogonis*; Corn: *Fusarium moniliforme* var. *subglutinans, Erwinia stewartii, Fusarium moniliforme, Gibberella zeae (Fusarium graminearum), Stenocarpella maydi (Diplodia/maydis), Pythium irregulare, Pythium debaryanum, Pythium graminicola, Pythium splendens, Pythium ultimum, Pythium aphanidermatum, Aspergillus flavus, Bipolaris maydis* O, T (*Cochliobolus heterostrophus*), *Helminthosporium carbonum* I, II & III (*Cochliobolus carbonum*), *Exserohilum turcicum* I, II & III, *Helminthosporium pedicellatum, Physoderma maydis, Phyllosticta maydis, Kabatiella maydis, Cercospora sorghi, Ustilago maydis, Puccinia sorghi, Puccinia polysora, Macrophomina phaseolina, Penicillium oxalicum, Nigrospora oryzae, Cladosporium herbarum, Curvularia lunata, Curvularia inaequalis, Curvularia pallescens, Clavibacter michiganense* subsp. *nebraskense, Trichoderma viride,* Maize Dwarf Mosaic Virus A & B, Wheat Streak Mosaic Virus, Maize Chlorotic Dwarf Virus, *Claviceps sorghi, Pseudonomas avenae, Erwinia chrysanthemi* pv. *zea, Erwinia carotovora,* Corn stunt spiroplasma, *Diplodia macrospora, Sclerophthora macrospora, Peronosclerospora sorghi, Peronosclerospora philippinensis, Peronosclerospora maydis, Peronosclerospora sacchari, Sphacelotheca reiliana, Physopella zeae, Cephalosporium maydis, Cephalosporium acremonium,* Maize Chlorotic Mottle Virus, High Plains Virus, Maize Mosaic Virus, Maize Rayado Fino Virus, Maize Streak Virus, Maize Stripe Virus, Maize Rough Dwarf Virus; Sorghum: *Exserohilum turcicum, Colletotrichum graminicola (Glomerella graminicola), Cercospora sorghi, Gloeocercospora sorghi, Ascochyta sorghina, Pseudomonas syringae* p.v. *syringae, Xanthomonas campestris* p.v. *holcicola, Pseudomonas andropogonis, Puccinia purpurea, Macrophomina phaseolina, Perconia circinata, Fusarium moniliforme, Alternaria alternata, Bipolaris sorghicola, Helminthosporium sorghicola, Curvularia lunata, Phoma insidiosa, Pseudomonas avenae (Pseudomonas alboprecipitans), Ramulispora sorghi, Ramulispora sorghicola, Phyllachara sacchari, Sporisorium reilianum (Sphacelotheca reiliana), Sphacelotheca cruenta, Sporisorium sorghi,* Sugarcane mosaic H, Maize Dwarf Mosaic Virus A & B, *Claviceps sorghi, Rhizoctonia solani, Acremonium strictum, Sclerophthona macrospora, Peronosclerospora sorghi, Peronosclerospora philippinensis, Sclerospora graminicola, Fusarium graminearum, Fusarium oxysporum, Pythium arrhenomanes, Pythium graminicola,* etc.

Nematodes include parasitic nematodes such as root knot, cyst, and lesion nematodes, including Heterodera and Globodera spp; particularly *Globodera rostochiensis* and *globodera pailida* (potato cyst nematodes); *Heterodera glycines* (soybean cyst nematode); *Heterodera schachtii* (beet cyst nematode); and *Heterodera avenae* (cereal cyst nematode).

Insect pests include insects selected from the orders Coleoptera, Diptera, Hymenoptera, Lepidoptera, Mallophaga, Homoptera, Hemiptera, Orthoptera, Thysanoptera, Dermaptera, Isoptera, Anoplura, Siphonaptera, Trichoptera, etc., particularly Coleoptera and Lepidoptera. Insect pests of the invention for the major crops include: Maize: *Ostrinia nubilalis*, European corn borer; *Agrotis ipsilon*, black cutworm; *Helicoverpa zea*, corn earworm; *Spodoptera frugiperda*, fall armyworm; *Diatraea grandiosella*, southwestern corn borer; *Elasmopalpus lignosellus*, lesser cornstalk borer; *Diatraea saccharalis*, surgarcane borer; *Diabrotica virgifera*, western corn rootworm; *Diabrotica longicornis barberi*, northern corn rootworm; *Diabrotica undecimpunctata howardi*, southern corn rootworm; Melanotus spp., wireworms; *Cyciocephala borealis*, northern masked chafer (white grub); *Cyclocephala immaculata*, southern masked chafer (white grub); *Popillia japonica*, Japanese beetle; *Chaetocnema pulicaria*, corn flea beetle; *Sphenophorus maidis*, maize billbug; *Rhopalosiphum maidis*, corn leaf aphid; *Anuraphis maidiradicis*, corn root aphid; *Blissus leucopterus leucopterus*, chinch bug; *Melanoplus femurrubrum*, redlegged grasshopper; *Melanoplus sanguinipes*, migratory grasshopper; *Hylemya platura*, seedcorn maggot; *Agromyza parvicornis*, corn blot leafminer; *Anaphothrips obscrurus*, grass thrips; *Solenopsis milesta*, thief ant; *Tetranychus urticae*, two spotted spider mite; Sorghum: *Chilo partellus*, sorghum borer; *Spodoptera frugiperaa*, fall armyworm; *Helicoverpa zea*, corn earworm; *Elasmopalpus lignosellus*, lesser cornstalk borer; *Feltia subterranea*, granulate cutworm; *Phyllophaga crinita*, white grub; Eleodes, Conoderus, and Aeolus spp., wireworms; *Oulema melanopus*, cereal leaf beetle; *Chaetocnema pulicaria*, corn flea beetle; *Sphenophorus maidis*, maize billbug; *Rhopalosiphum maidis*; corn leaf aphid; *Sipha flava*, yellow sugarcane aphid; *Blissus leucopterus leucopterus*, chinch bug; *Contarinia sorghicola*, sorghum midge; *Tetranychus cinnabarinus*, carmine spider mite; *Tetranychus urticae*, twospotted spider mite; Wheat: *Pseudaletia unipunctata*, army worm; *Spodoptera frugiperda*, fall armyworm, *Elasmopalpus lignosellus*, lesser cornstalk borer; *Agrotis orthogonia*, western cutworm; *Elasmopalpus lignosellus*, lesser cornstalk borer; *Oulema melanopus*, cereal leaf beetle; *Hypera punctata*, clover leaf weevil; *Diabrotica undecimpunctata howardi*, southern corn rootworm; Russian wheat aphid; *Schizaphis graminum*, greenbug; *Macrosiphum avenae*, English grain aphid; *Melanoplus femurrubrum*, redlegged grasshopper; *Melanoplus differentialis*, differential grasshopper; *Melanoplus sanguinipes*, migratory grasshopper; *Mayetiola destructor*, Hessian fly; *Sitodiplosis mosellana*, wheat midge; *Meromyza americana*, wheat stem maggot; *Hylemya coarctata*, wheat bulb fly; *Frankliniella fusca*, tobacco thrips; *Cephus cinctus*, wheat stem sawfly; *Aceria tulipae*, wheat curl mite; Sunflower: *Suleima helianthana*, sunflower bud moth; *Homoeosoma electellum*, sunflower moth; *zygogramma exclamationis*, sunflower beetle; *Bothyrus gibbosus*, carrot beetle; *Neolasioptera nurtfeidtiana*, sunflower seed midge; Cotton: *Heliothis virescens*, cotton budworm; *Helicoverpa zea*, cotton bollworm; *Spodoptera exigua*, beet armyworm;

*Pectinophora gossypiella*, pink bollworm; *Anthonomus grandis grandis*, boll weevil; *Aphis gossypii*, cotton aphid; *Pseudatomoscelis seriatus*, cotton fleahopper; *Trialeurodes abutilonea*, bandedwinged whitefly; *Lygus lineolaris*, tarnished plant bug; *Melanoplus femurrubrum*, redlegged grasshopper; *Melanoplus differentialis*, differential grasshopper; *Thrips tabaci*, onion thrips; *Franklinkiella fusca*, tobacco thrips; *Tetranychus cinnabarinus*, carmine spider mite; *Tetranychus urticae*, twospotted spider mite; Rice: *Diatraea saccharalis*, sugarcane borer; *Spodoptera frugiperda*, fall armyworm; *Helicoverpa zea*, corn earworm; *Colaspis brunnea*, grape colaspis; *Lissorhoptrus oryzophilus*, rice water weevil; *Sitophilus oryzae*, rice weevil; *Nephotettix nigropictus*, rice leafhopper; *Blissus leucopterus leucopterus*, chinch bug; *Acrosternum hilare*, green stink bug; Soybean: *Pseudoplusia includens*, soybean looper; *Anticarsia gemmatalis*, velvetbean caterpillar; *Plathypena scabra*, green cloverworm; *Ostrinia nubilalis*, European corn borer; *Agrotis ipsilon*, black cutworm; *Spodoptera exigua*, beet armyworm; *Heliothis virescens*, cotton budworm; *Helicoverpa zea*, cotton bollworm; *Epilachna varivestis*, Mexican bean beetle; *Myzus persicae*, green peach aphid; *Empoasca fabae*, potato leafhopper; *Acrostemum hilare*, green stink bug; *Melanoplus femurrubrum*, redlegged grasshopper; *Melanoplus differentialis*, differential grasshopper; *Hylemya platura*, seedcorn maggot, *Sericothrips variabilis*, soybean thrips; *Thrips tabaci*, onion thrips; *Tetranychus turkestani*, strawberry spider mite; *Tetranychus urticae*, twospotted spider mite; Barley: *Ostrinia nubilalis*, European corn borer; *Agrotis ipsilon*, black cutworm; *Schizaphis graminum*, greenbug; *Blissus leucopterus leucopterus*, chinch bug; *Acrosternum hilare*, green stink bug; *Euschistus servus*, brown stink bug; *Delia platura*, seedcorn maggot; *Mayetiola destructor*, Hessian fly; *Petrobia latens*, brown wheat mite; Oil Seed Rape: *Brevicoryne brassicae*, cabbage aphid; *Phyllotreta cruciferae*, Flea beetle; *Mamestra configurata*, Bertha armyworm; *Plutella xylostella*, Diamond-back moth; Delia ssp., Root maggots.

The following examples are offered by way of illustration, not by way of limitation.

EXPERIMENTAL

EXAMPLE 1

The rhm1 mutation confers recessive resistance to *Cochliobolus heterostrophus*, the causal agent of Southern Leaf Blight. RNA samples from rhm1 plants were analysed before and after inoculation with a pathogen. Results of the RNA sampling indicated that there were relatively few differences in gene expression, either before or after inoculation. Before inoculation, there were approximately 18 bands out of more than 8,000 bands that showed marked alteration and expression. After inoculation, there were 30 or so bands marked altered out of some 12,000 bands compared. Of these, approximately 19 were up-regulated and 11 down-regulated. Five of the 19 up-regulated bands represented the β-glucosidase gene. The five up-regulated bands do not easily distinguish the glu1 and glu2 isozymes. Thus, one or both of the isozymes may be up-regulated.

One of the up-regulated β-glucosidase bands was confirmed by a "poisoning" process. This involves repeating the PCR analysis of the mRNA (cDNA) samples from rhm1 and wildtype, but with unlabelled primers designed to an internal portion of the identified band. These internal primers are designed from existing published sequence for beta-glucosidase. If the band indeed represents beta-glucosidase, upon internal primer PCR amplification, the resulting unlabelled PCR product will eliminate the originally observed β-glucosidase band. Such was the case, thereby confirming it was β-glucosidase.

Messenger RNA abundance levels were determined using CuraGen mRNA profiling technology between two independent rhm1 alleles and their corresponding wildtype siblings. RNA was isolated from seedling leaves 24 hours after inoculation with *Cochliobolus heterostrophus* (*Bipolaris maydis*).

FIG. 1 shows that there was no average difference between either allele of rhm1 (865 and 1004) and their wildtype siblings in overall average mRNA expression following inoculation with *Bipolaris maydis*. A summation of mRNA (CuraGen band) expression changes that were either up or down regulated more than 1.4 fold for either of the two rhm1 alleles and their wildtype counterparts was made (sum), and average fold differences (ave) for all such genes in each genotype were calculated. What is apparent is that there is essentially no difference in average fold difference for either up-regulated or down-regulated genes between rhm1 and wildtype siblings. This result is significant because it shows that rhm1 and wildtype plants do not differ in their general defense posture as measured by mRNA abundance levels. It is known from other defense studies in plants, that resistant and susceptible plants can show marked differences in the level and timing of mRNA expression following pathogen ainoculation. This result provides a context that increases the apparent biological significance of the beta-glucosidase gene expression difference between rhm1 and wildtype. Namely, because the general gene expression and defense responses do not differ between rhm1 and wildtype, the few gene expression difference that do exist, foremost amongst them that for the beta-glucosidase gene, even more strongly argues that the higher beta-glucosidase expression in rhm1 is related to the resistance phenotype. Coupled with the apparent role of beta-glucosidase in the release of antimicrobial compounds from their glucosyl-conjugates, this strongly argues that beta-glucosidase can be used to control disease resistance in crop plants such as maize.

A mRNA northern timecourse has been completed following inoculation of rhm1 and wildtype siblings with *Cochliobolus heterostrophus*, a maize foliar pathogen. The northern clearly indicates that the amount of β-glucosidase expression is higher and longer sustained after inoculation in rhm1 (data not shown). This northern result confirms the CuraGen mRNA profiling observation.

The CuraGen profiling technology and subsequent Northern blot analysis using these tissues and treatments revealed that beta-glucosidase mRNA is more highly expressed in rhm1 mutants relative to wildtype. Few other gene expression differences (greater than plus or minus 1.4 fold) were found between rhm1 and wildtype. This indicated that the beta-glucosidase expression difference is significant and may be related to the phenotypic difference in resistance.

An analysis of free DIMBOA levels in rhm1 versus wildtype has been completed for all four available alleles (co-op, 865, 1004, and 994). Free DIMBOA is a product of β-glucosidase acting upon DIMBOA glucosides. Higher levels of free DIMBOA was observed for all four rhm1 alleles, with or without inoculation with *C. heterostrophus*, relative to the levels found in their corresponding wildtype siblings. For this experiment, the DIMBOA levels were collected 24 hours after inoculation. The higher the relative increase in free DIMBOA correlates with allelic strength. (The highest to lowest rhm1 allelic strength is 994>Coop>1004>865). The free DIMBOA results are presented in FIG. 2. A632 and A63 are wildtype controls for comparison.

EXAMPLE 2

Incorporation of β-glucosidase Sequence into Expression Vectors

Figure 3:
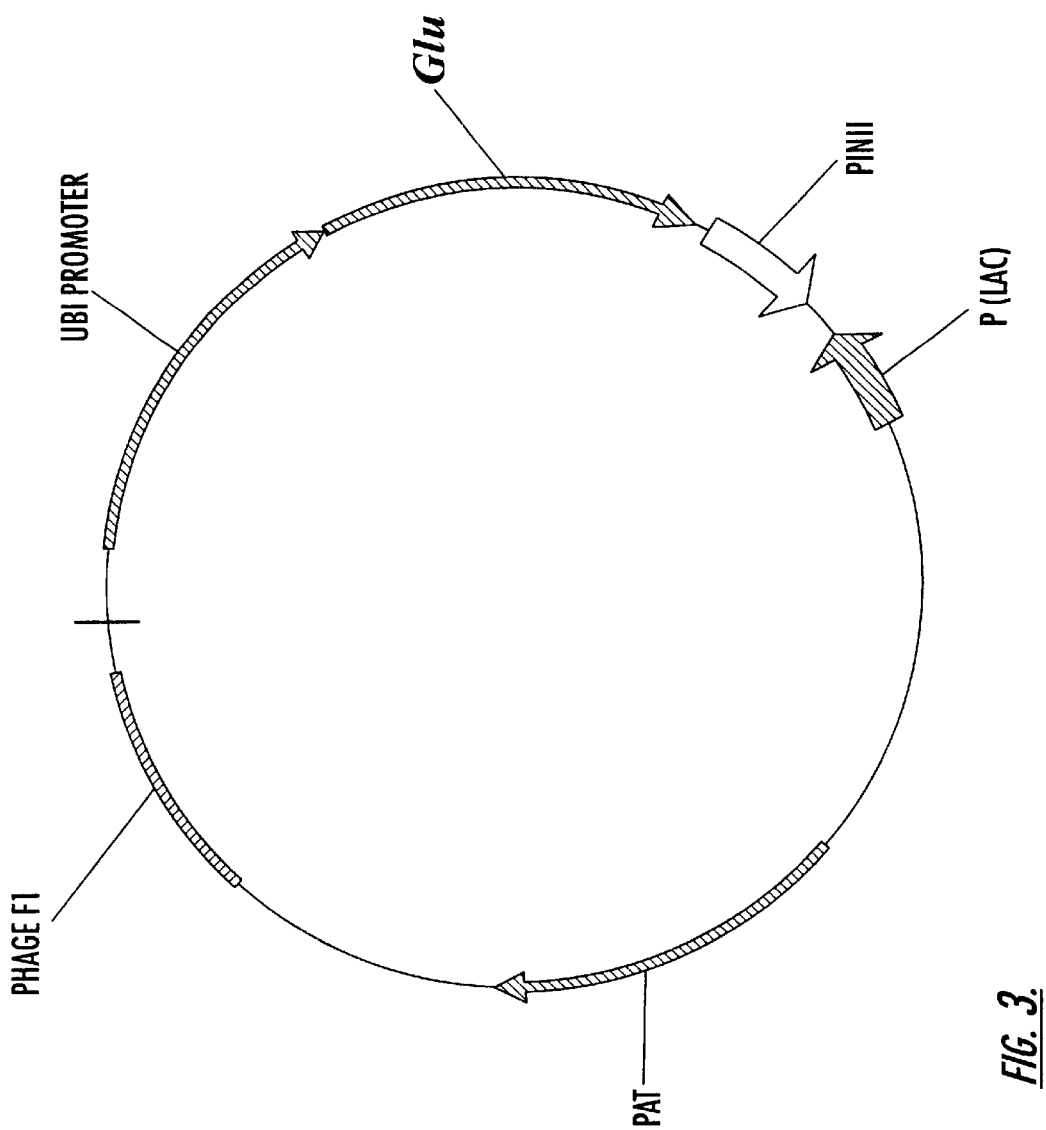
FIG. 3 provides a plasmid construct showing the Glu gene driven by the ubiquitin promoter.

Maize cDNA clones encoding the maize β-glucosidase genes were utilized (glu1: Acc. Nos . U44773 and U25157 and glu2: Acc. No. U44087). The glu genes were then cloned into plant expression constructs as shown in FIG. 3. A Bar gene or modified Pat gene is used as the selectable marker. Gene constructs have been introduced into corn by Agrobacterium-mediated transformation. More than 20 transformation events from each construct have been obtained. Effects of β-glucosidase expression on pathogen resistance will be analyzed.

EXAMPLE 3

Transformation and Regeneration of Transgenic Plants

Immature maize embryos from greenhouse donor plants are bombarded with a plasmid containing the nucleotide sequence encoding the β-glucosidase gene operably linked to a ubiquitin promoter. This plasmid also contains the selectable marker gene PAT (Wohlleben et al. (1988) *Gene* 70:25–37) that confers resistance to the herbicide Bialaphos (FIG. 3). Transformation is performed as follows. All media recipes are provided in tables 1–4.

Preparation of Target Tissue

The ears are surface sterilized in 30% Chlorox bleach plus 0.5% Micro detergent for 20 minutes, and rinsed two times with sterile water. The immature embryos are excised and placed embryo axis side down (scutellum side up), 25 embryos per plate, on 560Y medium (Table 4) for 4 hours and then aligned within the 2.5-cm target zone in preparation for bombardment.

Preparation of DNA

A plasmid vector comprising the β-glucosidase operably linked to a ubiquitin promoter is made. This plasmid DNA plus plasmid DNA containing a PAT selectable marker is precipitated onto 1.1 μm (average diameter) tungsten pellets using a $CaCl_2$ precipitation procedure as follows:

100 μl prepared tungsten particles in water
10 μl (1 μg) DNA in TrisEDTA buffer (1 μg total)
100 μl 2.5 M $CaCl_2$
10 μl 1 0.1 M spermidine Each reagent is added sequentially to the tungsten particle suspension, while maintained on the multitube vortexer. The final mixture is sonicated briefly and allowed to incubate under constant vortexing for 10 minutes. After the precipitation period, the tubes are centrifuged briefly, liquid removed, washed with 500 ml 100% ethanol, and centrifuged for 30 seconds. Again the liquid is removed, and 105 μl 100% ethanol is added to the final tungsten particle pellet. For particle gun bombardment, the tungsten/DNA particles are briefly sonicated and 10 μl spotted onto the center of each macrocarrier and allowed to dry about 2 minutes before bombardment.

Particle Gun Treatment

The sample plates are bombarded at level #4 in particle gun #HE34-1 or #HE34-2. All samples receive a single shot at 650 PSI, with a total of ten aliquots taken from each tube of prepared particles/DNA.

Subsequent Treatment

Following bombardment, the embryos are kept on 560Y medium (Table 4) for 2 days, then transferred to 560R selection medium (Table 3) containing 3 mg/liter Bialaphos, and subcultured every 2 weeks. After approximately 10 weeks of selection, selection-resistant callus clones are transferred to 288J medium (Table 2) to initiate plant regeneration. Following somatic embryo maturation (2–4 weeks), well-developed somatic embryos are transferred to medium for germination and transferred to the lighted culture room. Approximately 7–10 days later, developing plantlets are transferred to 272V hormone-free medium (Table 1) in tubes for 7–10 days until plantlets are well established. Plants are then transferred to inserts in flats (equivalent to 2.5" pot) containing potting soil and grown for 1 week in a growth chamber, subsequently grown an additional 1–2 weeks in the greenhouse, then transferred to classic 600 pots (1.6 gallon) and grown to maturity. Plants are monitored and scored for enhanced disease resistance or increased β-glucosidase activity.

TABLE 1. 272V

| Ingredient | Amount | Unit |
| --- | --- | --- |
| D-I $H_2O$ | 950.000 | Ml |
| MS Salts (GIBCO 11117-074) | 4.300 | G |
| Myo-Inositol | 0.100 | G |
| MS Vitamins Stock Solution ## | 5.000 | Ml |
| Sucrose | 40.000 | G |
| Bacto-Agar @ | 6.000 | G |

Directions:
@ = Add after bringing up to volume
Dissolve ingredients in polished D-I $H_2O$ in sequence
Adjust to pH 5.6
Bring up to volume with polished D-I $H_2O$ after adjusting pH
Sterilize and cool to 60° C.
## = Dissolve 0.100 g of Nicotinic Acid; 0.020 g of Thiamine.HCL; 0.100 g of Pyridoxine.HCL; and 0.400 g of Glycine in 875.00 ml of polished D-I $H_2O$ in sequence. Bring up to volume with polished D-I $H_2O$. Make in 400 ml portions. Thiamine.HCL & Pyridoxine.HCL are in Dark Desiccator. Store for one month, unless contamination or precipitation occurs, then make fresh stock.
Total Volume (L) = 1.00

TABLE 2.288J

| Ingredient | Amount | Unit |
| --- | --- | --- |
| D-I $H_2O$ | 950.000 | Ml |
| MS Salts | 4.300 | G |
| Myo-Inositol | 0.100 | G |
| MS Vitamins Stock Solution ## | 5.000 | Ml |
| Zeatin .5 mg/ml | 1.000 | Ml |
| Sucrose | 60.000 | G |
| Gelrite @ | 3.000 | G |
| Indoleacetic Acid 0.5 mg/ml # | 2.000 | Ml |
| 0.1 mM Abscisic Acid | 1.000 | Ml |
| Bialaphos 1 mg/ml # | 3.000 | Ml |

Directions:
@ = Add after bringing up to volume
Dissolve ingredients in polished D-I $H_2O$ in sequence
Adjust to pH 5.6
Bring up to volume with polished D-I $H_2O$ after adjusting pH
Sterilize and cool to 60° C.
Add 3.5 g/L of Gelrite for cell biology.
## = Dissolve 0.100 g of Nicotinic Acid; 0.020 g of Thiamine.HCL; 0.100 g of Pyridoxine.HCL; and 0.400 g of Glycine in 875.00 ml of polished D-I $H_2O$ in sequence. Bring up to volume with polished D-I $H_2O$. Make in 400 ml portions. Thiamine.HCL & Pyridoxine.HCL are in Dark Desiccator. Store for one month, unless contamination or precipitation occurs, then make fresh stock.
Total Volume (L) = 1.00

TABLE 3.560R

| Ingredient | Amount | Unit |
| --- | --- | --- |
| D-I Water, Filtered | 950.000 | Ml |
| CHU (N6) Basal Salts (SIGMA C-1416) | 4.000 | G |
| Eriksson's Vitamin Mix (1000X SIGMA-1511 | 1.000 | Ml |
| Thiamine.HCL 0.4 mg/ml | 1.250 | Ml |
| Sucrose | 30.000 | G |
| 2, 4-D 0.5 mg/ml | 4.000 | Ml |
| Gelrite @ | 3.000 | G |
| Silver Nitrate 2 mg/ml # | 0.425 | Ml |
| Bialaphos 1 mg/ml # | 3.000 | Ml |

Directions:
@ = Add after bringing up to volume
# = Add after sterilizing and cooling to temp.
Dissolve ingredients in D-I $H_2O$ in sequence
Adjust to pH 5.8 with KOH
Bring up to volume with D-I $H_2O$
Sterilize and cool to room temp.
Total Volume (L) = 1.00

TABLE 4.560Y

| Ingredient | Amount | Unit |
| --- | --- | --- |
| D-I Water, Filtered | 950.000 | Ml |
| CHU (N6) Basal Salts (SIGMA C-1416) | 4.000 | G |
| Eriksson's Vitamin Mix (1000X SIGMA-1511 | 1.000 | Ml |
| Thiamine.HCL 0.4 mg/ml | 1.250 | Ml |
| Sucrose | 120.000 | G |
| 2,4-D 0.5 mg/ml | 2.000 | Ml |
| L-Proline | 2.880 | G |
| Gelrite @ | 2.000 | G |
| Silver Nitrate 2 mg/ml # | 4.250 | Ml |

Directions:
@ = Add after bringing up to volume
# = Add after sterilizing and cooling to temp.
Dissolve ingredients in D-I $H_2O$ in sequence
Adjust to pH 5.8 with KOH
Bring up to volume with D-I $H_2O$
Sterilize and cool to room temp.
 Autoclave less time because of increased sucrose 
Total Volume (L) = 1 .00

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. A method for enhancing disease resistance in a plant, said method comprising stably incorporating into the genome of said plant a DNA construct comprising a nucleotide sequence operably linked to a promoter that drives expression in a plant cell, wherein said nucleotide sequence is selected from the group consisting of:
   a) a nucleic acid molecule comprising the nucleotide sequence of SEQ ID NO:1; and,
   b) a nucleic acid molecule encoding the amino acid sequence of SEQ ID NO:2;
   contacting said plant with a pathogenic organism; and, enhancing the disease resistance of said plant.

2. The method of claim 1, wherein said plant is a monocot.
3. The method of claim 1, wherein said plant is a dicot.
4. The method of claim 2, wherein said plant is maize.
5. The method of claim 1, wherein said promoter is a constitutive promoter.
6. The method of claim 1, wherein said promoter is a tissue-preferred promoter.
7. The method of claim 1, wherein said promoter is an inducible promoter.
8. A method for enhancing disease resistance in a plant, said method comprising stably incorporating into the genome of said plant a DNA construct comprising a nucleotide sequence operably linked to a promoter that drives expression in a plant cell, wherein said nucleotide sequence is selected from the group consisting of:
   a) a nucleic acid molecule comprising the nucleotide sequence of SEQ ID NO:3; and,
   b) a nucleic acid molecule encoding the amino acid sequence of SEQ ID NO:4;
   contacting said plant with a pathogenic organism; and, enhancing the disease resistance of said plant.

9. The method of claim 8, wherein said plant is a monocot.
10. The method of claim 8, wherein said plant is a dicot.
11. The method of claim 9, wherein said monocot is maize.
12. The method of claim 8, wherein said promoter is a constitutive promoter.
13. The method of claim 8, wherein said promoter is a tissue-preferred promoter.
14. The method of claim 8, wherein said promoter is an inducible promoter.
15. A method for enhancing disease resistance in a plant, said method comprising stably incorporating into the genome of said plant a DNA construct comprising a nucleotide sequence operably linked to a promoter that drives expression in a plant cell, wherein said nucleotide sequence has at least 90% sequence identity to the sequence of SEQ ID NO:1, wherein said sequence encodes a polypeptide that catalyzes the hydrolysis of a glycosidic linkage in DIMBOA-glu; contacting said plant with a pathogenic organism; and, enhancing the disease resistance of said plant.

16. A method for enhancing disease resistance in a plant, said method comprising stably incorporating into the genome of said plant a DNA construct comprising a nucleotide sequence operably linked to a promoter that drives expression in a plant cell, wherein said nucleotide sequence has at least 90% sequence identity to the sequence of SEQ ID NO:3, wherein said sequence encodes a polypeptide that catalyzes the hydrolysis of a glycosidic linkage in DIMBOA-glu and contacting said plant with a pathogenic organism; and, enhancing the disease resistance of said plant.

17. The method of claim 15, wherein said plant is a monocot.

18. The method of claim 15, wherein said plant is a dicot.

19. The method of claim 17, wherein said monocot is maize.

20. The method of claim 15, wherein said promoter is a constitutive promoter.

21. The method of claim 15, wherein said promoter is a tissue-preferred promoter.

22. The method of claim 15, wherein said promoter is an inducible promoter.

23. The method of claim 15, wherein said nucleotide sequence has at least 95% sequence identity to the sequence of SEQ ID NO:1, wherein said sequence encodes a polypeptide that catalyzes the hydrolysis of a glycosidic linkage in DIMBOA-glu.

24. The method of claim 23, wherein said plant is a monocot.

25. The method of claim 23, wherein said plant is a dicot.

26. The method of claim 24, wherein said monocot is maize.

27. The method of claim 23, wherein said promoter is a constitutive promoter.

28. The method of claim 23, wherein said promoter is a tissue-preferred promoter.

29. The method of claim 23, wherein said promoter is an inducible promoter.

30. The method of claim 16, wherein said plant is a monocot.

31. The method of claim 16, wherein said plant is a dicot.

32. The method of claim 30, wherein said monocot is maize.

33. The method of claim 16, wherein said promoter is a constitutive promoter.

34. The method of claim 16, wherein said promoter is a tissue-preferred promoter.

35. The method of claim 16, wherein said promoter is an inducible promoter.

36. The method of claim 16, wherein said nucleotide sequence has at least 95% sequence identity to the sequence of SEQ ID NO:3, wherein said sequence encodes a polypeptide that catalyzes the hydrolysis of a glycosidic linkage in DIMBOA-glu.

37. The method of claim 36, wherein said plant is a monocot.

38. The method of claim 36, wherein said plant is a dicot.

39. The method of claim 37, wherein said monocot is maize.

40. The method of claim 36, wherein said promoter is a constitutive promoter.

41. The method of claim 36, wherein said promoter is a tissue-preferred promoter.

42. The method of claim 36 wherein said promoter is an inducible promoter.

43. A method for enhancing disease resistance in a plant cell, said method comprising stably incorporating into the genome of said plant cell a DNA construct comprising a nucleotide sequence operably linked to a promoter that drives expression in the plant cell, wherein said nucleotide sequence is selected from the group consisting of:
   a) a nucleic acid molecule comprising the nucleotide sequence of SEQ ID NO:1; and,
   b) a nucleic acid molecule encoding the amino acid sequence or SEQ ID NO:2;
   contacting said plant cell with a pathogenic organism; and, enhancing the disease resistance of said plant cell.

44. The method of claim 43, wherein said plant cell is from a monocot.

45. The method of claim 43, wherein said plant cell is from a dicot.

46. The method of claim 44, wherein said monocot is maize.

47. The method of claim 43, wherein said promoter is a constitutive promoter.

48. The method of claim 43, wherein said promoter is a tissue-preferred promoter.

49. The method of claim 43, wherein said promoter is an inducible promoter.

50. A method for enhancing disease resistance in a plant cell, said method comprising stably incorporating into the genome of said plant cell a DNA construct comprising a nucleotide sequence operably linked to a promoter that drives expression in the plant cell, wherein said nucleotide sequence is selected from the group consisting of:
   a) a nucleic acid molecule comprising the nucleotide sequence of SEQ ID NO:3; and,
   b) a nucleic acid molecule encoding the amino acid sequence of SEQ ID NO:4;
   contacting said plant cell with a pathogenic organism; and, enhancing the disease resistance of said plant cell.

51. The method of claim 50, wherein said plant cell is from a monocot.

52. The method of claim 50, wherein said plant cell is from a dicot.

53. The method of claim 51, wherein said monocot is maize.

54. The method of claim 50, wherein said promoter is a constitutive promoter.

55. The method of claim 50, wherein said promoter is a tissue-preferred promoter.

56. The method of claim 50, wherein said promoter is an inducible promoter.

57. A method for enhancing disease resistance in a plant cell, said method comprising stably incorporating into the genome of said plant cell a DNA construct comprising a nucleotide sequence operably linked to a promoter that drives expression in the plant cell, wherein said nucleotide sequence has at least 90% sequence identity to the sequence of SEQ ID NO:3, wherein said sequence encodes a polypeptide that catalyzes the hydrolysis of a glycosidic linkage in DIMBOA-glu, and contacting said plant cell with a pathogenic organism; and, enhancing the disease resistance of said plant cell.

58. The method of claim 57, wherein said plant cell is from a monocot.

59. The method of claim 57, wherein said plant cell is from a dicot.

60. The method of claim 58, wherein said monocot is maize.

61. The method of claim 57, wherein said promoter is a constitutive promoter.

62. The method of claim 57, wherein said promoter is a tissue-preferred promoter.

63. The method of claim 57, wherein said promoter is an inducible promoter.

64. The method of claim 57, wherein said nucleotide sequence has at least 95% sequence identity to the sequence of SEQ ID NO:3, wherein said sequence encodes a polypeptide that catalyzes the hydrolysis of a glycosidic linkage in DIMBOA-glu.

65. The method of claim 64, wherein said plant cell is from a monocot.

66. The method of claim 64, wherein said plant cell is from a dicot.

67. The method of claim 65, wherein said monocot is maize.

68. The method of claim 64, wherein said promoter is a constitutive promoter.

69. The method of claim 64, wherein said promoter is a tissue-preferred promoter.

70. The method of claim 64, wherein said promoter is an inducible promoter.

71. A method for enhancing disease resistance in a plant cell, said method comprising stably incorporating into the genome of said plant cell a DNA construct comprising a nucleotide sequence operably linked to a promoter that drives expression in the plant cell, wherein said nucleotide sequence has at least 90% sequence identity to the sequence of SEQ ID NO:1, wherein said sequence encodes a polypeptide that catalyzes the hydrolysis of a glycosidic linkage in DIMBOA-glu, and contacting said plant cell with a pathogenic organism; and, enhancing the disease resistance of said plant cell.

72. The method of claim 71, wherein said plant cell is from a monocot.

73. The method of claim 71, wherein said plant cell is from a dicot.

74. The method of claim 72, wherein said monocot is maize.

75. The method of claim 71, wherein said promoter is a constitutive promoter.

76. The method of claim 71, wherein said promoter is a tissue-preferred promoter.

77. The method of claim 71, wherein said promoter is an inducible promoter.

78. The method of claim 71, wherein said nucleotide sequence has at least 95% sequence identity to the sequence of SEQ ID NO:1, wherein said sequence encodes a polypeptide that catalyzes the hydrolysis of a glycosidic linkage in DIMBOA-glu.

79. The method of claim 78, wherein said plant cell is from a monocot.

80. The method of claim 78, wherein said plant cell is from a dicot.

81. The method of claim 79, wherein said monocot is maize.

82. The method of claim 78, wherein said promoter is a constitutive promoter.

83. The method of claim 78, wherein said promoter is a tissue-preferred promoter.

84. The method of claim 78, wherein said promoter is an inducible promoter.

\* \* \* \* \*

SEQUENCE LISTING

<160> NUMBER OF SEQ ID NOS: 4

<210> SEQ ID NO 1
<211> LENGTH: 1931
<212> TYPE: DNA
<213> ORGANISM: Zea mays
<220> FEATURE:
<221> NAME/KEY: misc_feature
<222> LOCATION: (0)...(0)
<223> OTHER INFORMATION: Glu1 (Genbank Accession Number U25157)
<221> NAME/KEY: CDS
<222> LOCATION: (32)...(1729)

<400> SEQUENCE: 1

```
tagttctagc tagctagcaa aggggggaa a atg gct ccg ctt ctc gct gct       52
                                 Met Ala Pro Leu Leu Ala Ala
                                  1               5 gcc atg aac cac gct gca gcc cat cct ggc ctt agg agc cac cta gta    100
Ala Met Asn His Ala Ala Ala His Pro Gly Leu Arg Ser His Leu Val
         10                  15                  20 gga ccc aac aat gag agt ttc tca cgg cac cac ctg ccg tct tct tct    148
Gly Pro Asn Asn Glu Ser Phe Ser Arg His His Leu Pro Ser Ser Ser
 25                  30                  35 cca cag agc agc aag cga agg tgt aac ctt agc ttt act aca cga tct    196
Pro Gln Ser Ser Lys Arg Arg Cys Asn Leu Ser Phe Thr Thr Arg Ser
 40                  45                  50                  55 gca aga gta ggc agc caa aat gga gtc caa atg ttg agc ccc tcg gaa    244
Ala Arg Val Gly Ser Gln Asn Gly Val Gln Met Leu Ser Pro Ser Glu
                 60                  65                  70 atc cca caa agg gac tgg ttc ccc tct gac ttc acc ttc ggt gcc gcc    292
Ile Pro Gln Arg Asp Trp Phe Pro Ser Asp Phe Thr Phe Gly Ala Ala
             75                  80                  85 act tca gcg tac caa att gaa ggt gct tgg aat gaa gat gga aag ggg    340
```

```
                     Thr Ser Ala Tyr Gln Ile Glu Gly Ala Trp Asn Glu Asp Gly Lys Gly
                              90                  95                 100 gaa agc aac tgg gat cac ttc tgc cac aat cat ccg gaa agg ata ctg           388
Glu Ser Asn Trp Asp His Phe Cys His Asn His Pro Glu Arg Ile Leu
        105                 110                 115 gac ggg agc aat tca gac att gga gcg aat tcg tat cat atg tac aaa           436
Asp Gly Ser Asn Ser Asp Ile Gly Ala Asn Ser Tyr His Met Tyr Lys
120                 125                 130                 135 acg gac gtc aga ttg ctc aag gaa atg ggc atg gac gca tat agg ttc           484
Thr Asp Val Arg Leu Leu Lys Glu Met Gly Met Asp Ala Tyr Arg Phe
                140                 145                 150 tct atc tct tgg ccc aga ata ctg ccg aag gga acc aaa gaa gga ggt           532
Ser Ile Ser Trp Pro Arg Ile Leu Pro Lys Gly Thr Lys Glu Gly Gly
            155                 160                 165 att aac cct gat ggc atc aag tac tac aga aac ctc atc aac ttg ttg           580
Ile Asn Pro Asp Gly Ile Lys Tyr Tyr Arg Asn Leu Ile Asn Leu Leu
        170                 175                 180 ctg gaa aac ggc ata gag cca tat gta aca att ttc cac tgg gat gta           628
Leu Glu Asn Gly Ile Glu Pro Tyr Val Thr Ile Phe His Trp Asp Val
    185                 190                 195 cct caa gca cta gaa gag aag tac ggc ggc ttc cta gat aag agt cat           676
Pro Gln Ala Leu Glu Glu Lys Tyr Gly Gly Phe Leu Asp Lys Ser His
200                 205                 210                 215 aag agc att gta gaa gat tac acc tac ttc gct aag gtg tgc ttt gat           724
Lys Ser Ile Val Glu Asp Tyr Thr Tyr Phe Ala Lys Val Cys Phe Asp
                220                 225                 230 aac ttc ggc gac aag gtg aag aat tgg ttg acc ttt aat gag ccc cag           772
Asn Phe Gly Asp Lys Val Lys Asn Trp Leu Thr Phe Asn Glu Pro Gln
            235                 240                 245 aca ttt act tcc ttt tcc tac gga act ggg gtc ttt gcc cca ggt cgg           820
Thr Phe Thr Ser Phe Ser Tyr Gly Thr Gly Val Phe Ala Pro Gly Arg
        250                 255                 260 tgc tca cct gga cta gac tgt gcc tac cca act ggg aat tca ctc gtc           868
Cys Ser Pro Gly Leu Asp Cys Ala Tyr Pro Thr Gly Asn Ser Leu Val
    265                 270                 275 gag cct tac act gct ggc cat aac att ctc cta gcc cac gct gag gct           916
Glu Pro Tyr Thr Ala Gly His Asn Ile Leu Leu Ala His Ala Glu Ala
280                 285                 290                 295 gtt gat ctt tac aac aag cat tac aag cgc gac gac acc cgc ata ggg           964
Val Asp Leu Tyr Asn Lys His Tyr Lys Arg Asp Asp Thr Arg Ile Gly
                300                 305                 310 ctt gcg ttt gac gta atg ggt cgt gtg cca tac gga aca tcg ttt ctg          1012
Leu Ala Phe Asp Val Met Gly Arg Val Pro Tyr Gly Thr Ser Phe Leu
            315                 320                 325 gat aaa cag gcc gaa gaa agg tca tgg gac atc aac cta gga tgg ttc          1060
Asp Lys Gln Ala Glu Glu Arg Ser Trp Asp Ile Asn Leu Gly Trp Phe
        330                 335                 340 tta gag cca gtg gtt cgt ggt gac tac ccc ttc tcc atg aga tca ttg          1108
Leu Glu Pro Val Val Arg Gly Asp Tyr Pro Phe Ser Met Arg Ser Leu
    345                 350                 355 gct agg gaa cga cta ccc ttc ttc aag gac gag cag aag gag aag ctc          1156
Ala Arg Glu Arg Leu Pro Phe Phe Lys Asp Glu Gln Lys Glu Lys Leu
360                 365                 370                 375 gcc ggt tcc tat aac atg ttg ggg tta aac tac tac acc tca cgg ttc          1204
Ala Gly Ser Tyr Asn Met Leu Gly Leu Asn Tyr Tyr Thr Ser Arg Phe
                380                 385                 390 tcc aaa aac atc gac atc tca cca aac tac tca cct gtg ctc aac act          1252
Ser Lys Asn Ile Asp Ile Ser Pro Asn Tyr Ser Pro Val Leu Asn Thr
            395                 400                 405
```

-continued

```
gac gac gcc tac gcc agt caa gaa gtt aac ggg cct gac ggg aag ccc      1300
Asp Asp Ala Tyr Ala Ser Gln Glu Val Asn Gly Pro Asp Gly Lys Pro
            410                 415                 420 att ggt cct cct atg gga aat cca tgg atc tac atg tac cct gag ggc      1348
Ile Gly Pro Pro Met Gly Asn Pro Trp Ile Tyr Met Tyr Pro Glu Gly
    425                 430                 435 ttg aag gat ctc ctt atg ata atg aag aac aaa tac gga aac cca cct      1396
Leu Lys Asp Leu Leu Met Ile Met Lys Asn Lys Tyr Gly Asn Pro Pro
440                 445                 450                 455 atc tac atc acc gag aac gga atc ggg gat gtt gat acc aaa gag aca      1444
Ile Tyr Ile Thr Glu Asn Gly Ile Gly Asp Val Asp Thr Lys Glu Thr
                460                 465                 470 cct cta ccc atg gag gct gcc tta aat gac tac aaa agg cta gat tac      1492
Pro Leu Pro Met Glu Ala Ala Leu Asn Asp Tyr Lys Arg Leu Asp Tyr
            475                 480                 485 atc cag cgc cac atc gct act ctt aag gaa tca ata gac ttg gga tca      1540
Ile Gln Arg His Ile Ala Thr Leu Lys Glu Ser Ile Asp Leu Gly Ser
        490                 495                 500 aat gtg caa ggc tac ttc gct tgg tct ctg ctg gac aac ttt gaa tgg      1588
Asn Val Gln Gly Tyr Phe Ala Trp Ser Leu Leu Asp Asn Phe Glu Trp
505                 510                 515 ttt gcc ggc ttc acc gaa cgt tat ggc att gtc tac gtc gac cgc aac      1636
Phe Ala Gly Phe Thr Glu Arg Tyr Gly Ile Val Tyr Val Asp Arg Asn
520                 525                 530                 535 aat aac tgc acg cgc tac atg aag gag tct gcc aag tgg ttg aaa gag      1684
Asn Asn Cys Thr Arg Tyr Met Lys Glu Ser Ala Lys Trp Leu Lys Glu
                540                 545                 550 ttc aac acc gcg aaa aag ccc agc aag aag att ctt acg cca gct         1729
Phe Asn Thr Ala Lys Lys Pro Ser Lys Lys Ile Leu Thr Pro Ala
            555                 560                 565 taaaaatcgg gggcctcatg atgtgggtgc agcccataaa aacctgtgtg gtttggaacc    1789
gaagattttc tcttttttt ctgccacgag aggttctctg gaggcatact ctccagcacc     1849
gtggctaata acgcgttgtt ccaattcagt ctggccttgt catgcatgca ataaataaag    1909
tgatgggttt ccctgtttca at                                             1931

<210> SEQ ID NO 2
<211> LENGTH: 566
<212> TYPE: PRT
<213> ORGANISM: Zea mays

<400> SEQUENCE: 2

Met Ala Pro Leu Leu Ala Ala Met Asn His Ala Ala His Pro
1               5                   10                  15

Gly Leu Arg Ser His Leu Val Gly Pro Asn Asn Glu Ser Phe Ser Arg
            20                  25                  30

His His Leu Pro Ser Ser Ser Pro Gln Ser Ser Lys Arg Arg Cys Asn
        35                  40                  45

Leu Ser Phe Thr Thr Arg Ser Ala Arg Val Gly Ser Gln Asn Gly Val
    50                  55                  60

Gln Met Leu Ser Pro Ser Glu Ile Pro Gln Arg Asp Trp Phe Pro Ser
65                  70                  75                  80

Asp Phe Thr Phe Gly Ala Ala Thr Ser Ala Tyr Gln Ile Glu Gly Ala
                85                  90                  95

Trp Asn Glu Asp Gly Lys Gly Glu Ser Asn Trp Asp His Phe Cys His
            100                 105                 110

Asn His Pro Glu Arg Ile Leu Asp Gly Ser Asn Ser Asp Ile Gly Ala
        115                 120                 125
```

-continued

```
Asn Ser Tyr His Met Tyr Lys Thr Asp Val Arg Leu Leu Lys Glu Met
    130                 135                 140
Gly Met Asp Ala Tyr Arg Phe Ser Ile Ser Trp Pro Arg Ile Leu Pro
145                 150                 155                 160
Lys Gly Thr Lys Glu Gly Gly Ile Asn Pro Asp Gly Ile Lys Tyr Tyr
                165                 170                 175
Arg Asn Leu Ile Asn Leu Leu Glu Asn Gly Ile Glu Pro Tyr Val
                180                 185                 190
Thr Ile Phe His Trp Asp Val Pro Gln Ala Leu Glu Glu Lys Tyr Gly
                195                 200                 205
Gly Phe Leu Asp Lys Ser His Lys Ser Ile Val Glu Asp Tyr Thr Tyr
    210                 215                 220
Phe Ala Lys Val Cys Phe Asp Asn Phe Gly Asp Lys Val Lys Asn Trp
225                 230                 235                 240
Leu Thr Phe Asn Glu Pro Gln Thr Phe Thr Ser Phe Ser Tyr Gly Thr
                245                 250                 255
Gly Val Phe Ala Pro Gly Arg Cys Ser Pro Gly Leu Asp Cys Ala Tyr
                260                 265                 270
Pro Thr Gly Asn Ser Leu Val Glu Pro Tyr Thr Ala Gly His Asn Ile
                275                 280                 285
Leu Leu Ala His Ala Glu Ala Val Asp Leu Tyr Asn Lys His Tyr Lys
    290                 295                 300
Arg Asp Asp Thr Arg Ile Gly Leu Ala Phe Asp Val Met Gly Arg Val
305                 310                 315                 320
Pro Tyr Gly Thr Ser Phe Leu Asp Lys Gln Ala Glu Glu Arg Ser Trp
                325                 330                 335
Asp Ile Asn Leu Gly Trp Phe Leu Glu Pro Val Val Arg Gly Asp Tyr
                340                 345                 350
Pro Phe Ser Met Arg Ser Leu Ala Arg Glu Arg Leu Pro Phe Phe Lys
                355                 360                 365
Asp Glu Gln Lys Glu Lys Leu Ala Gly Ser Tyr Asn Met Leu Gly Leu
    370                 375                 380
Asn Tyr Tyr Thr Ser Arg Phe Ser Lys Asn Ile Asp Ile Ser Pro Asn
385                 390                 395                 400
Tyr Ser Pro Val Leu Asn Thr Asp Asp Ala Tyr Ala Ser Gln Glu Val
                405                 410                 415
Asn Gly Pro Asp Gly Lys Pro Ile Gly Pro Pro Met Gly Asn Pro Trp
                420                 425                 430
Ile Tyr Met Tyr Pro Glu Gly Leu Lys Asp Leu Leu Met Ile Met Lys
                435                 440                 445
Asn Lys Tyr Gly Asn Pro Pro Ile Tyr Ile Thr Glu Asn Gly Ile Gly
    450                 455                 460
Asp Val Asp Thr Lys Glu Thr Pro Leu Pro Met Glu Ala Ala Leu Asn
465                 470                 475                 480
Asp Tyr Lys Arg Leu Asp Tyr Ile Gln Arg His Ile Ala Thr Leu Lys
                485                 490                 495
Glu Ser Ile Asp Leu Gly Ser Asn Val Gln Gly Tyr Phe Ala Trp Ser
                500                 505                 510
Leu Leu Asp Asn Phe Glu Trp Phe Ala Gly Phe Thr Glu Arg Tyr Gly
    515                 520                 525
Ile Val Tyr Val Asp Arg Asn Asn Asn Cys Thr Arg Tyr Met Lys Glu
530                 535                 540
```

```
Ser Ala Lys Trp Leu Lys Glu Phe Asn Thr Ala Lys Lys Pro Ser Lys
545                 550                 555                 560

Lys Ile Leu Thr Pro Ala
                565

<210> SEQ ID NO 3
<211> LENGTH: 1931
<212> TYPE: DNA
<213> ORGANISM: Zea mays
<220> FEATURE:
<221> NAME/KEY: misc_feature
<222> LOCATION: (0)...(0)
<223> OTHER INFORMATION: glu2 (Genbank Accession Number U44087)
<221> NAME/KEY: CDS
<222> LOCATION: (30)...(1721)

<400> SEQUENCE: 3
aaaactctag ctagctagca gggggggaa atg gct cca ctt ctc gcc gca gcc         53
                                Met Ala Pro Leu Leu Ala Ala Ala
                                  1               5 atg aac cac gct gcc cat cca gtc ctt aga agc cat cta gga ccc aac        101
Met Asn His Ala Ala His Pro Val Leu Arg Ser His Leu Gly Pro Asn
 10              15                  20 aat gag agt ttc tca cga cac cac cta tct tct tca ccg caa agc agt        149
Asn Glu Ser Phe Ser Arg His His Leu Ser Ser Ser Pro Gln Ser Ser
 25                  30                  35                  40 aag cga agg ttt aac ctt agc ttt acg cca cga tct gca aga gta ggc        197
Lys Arg Arg Phe Asn Leu Ser Phe Thr Pro Arg Ser Ala Arg Val Gly
                 45                  50                  55 aat caa aat gga gtc caa ttg ttg agc cct tcg gaa atc cct cga agg        245
Asn Gln Asn Gly Val Gln Leu Leu Ser Pro Ser Glu Ile Pro Arg Arg
             60                  65                  70 gac tgg ttc ccc tct gac ttc atc ttt ggt gcc gcc act tca gcg tac        293
Asp Trp Phe Pro Ser Asp Phe Ile Phe Gly Ala Ala Thr Ser Ala Tyr
         75                  80                  85 caa att gaa ggt gct tgg aac gaa gat gga aag ggg gaa agc aat tgg        341
Gln Ile Glu Gly Ala Trp Asn Glu Asp Gly Lys Gly Glu Ser Asn Trp
     90                  95                 100 gat cac ttc tgc cac aat ttt ccg gaa agg ata atg gac ggg agc aat        389
Asp His Phe Cys His Asn Phe Pro Glu Arg Ile Met Asp Gly Ser Asn
105                 110                 115                 120 gca gac att gga gcg aat tcg tac cat atg tac aaa acg gat gtc aga        437
Ala Asp Ile Gly Ala Asn Ser Tyr His Met Tyr Lys Thr Asp Val Arg
                125                 130                 135 ttg ctg aag gaa atg ggc atg gac gca tat agg ttc tct atc tct tgg        485
Leu Leu Lys Glu Met Gly Met Asp Ala Tyr Arg Phe Ser Ile Ser Trp
            140                 145                 150 cct aga ata ctg cct aag gga acg gtc gaa gga ggt att aac cag gat        533
Pro Arg Ile Leu Pro Lys Gly Thr Val Glu Gly Gly Ile Asn Gln Asp
        155                 160                 165 ggc atc gat tac tac aaa agg ctc atc aac ttg ttg cta gag aat ggc        581
Gly Ile Asp Tyr Tyr Lys Arg Leu Ile Asn Leu Leu Leu Glu Asn Gly
    170                 175                 180 ata gag cca tat gta aca att ttc cac tgg gat gtc cct caa gca cta        629
Ile Glu Pro Tyr Val Thr Ile Phe His Trp Asp Val Pro Gln Ala Leu
185                 190                 195                 200 gaa gag aag tac ggc gga ttc tta gat aag act cag aag agg att gta        677
Glu Glu Lys Tyr Gly Gly Phe Leu Asp Lys Thr Gln Lys Arg Ile Val
                205                 210                 215 aat gat tac aaa aac ttc gct aag gtg tgc ttc gac aac ttt ggt gac        725
Asn Asp Tyr Lys Asn Phe Ala Lys Val Cys Phe Asp Asn Phe Gly Asp
            220                 225                 230
```

```
aag gtg aag aat tgg ttg acc ttt aat gag ccc cag aca ttt act tca      773
Lys Val Lys Asn Trp Leu Thr Phe Asn Glu Pro Gln Thr Phe Thr Ser
        235                 240                 245 ttt tcc tat gga acc ggg gtc ttt gcc cca gga cga tgc tca ccg gga      821
Phe Ser Tyr Gly Thr Gly Val Phe Ala Pro Gly Arg Cys Ser Pro Gly
    250                 255                 260 cta gac tgt gcc atc cca act ggg aat tca ctc gtc gaa cct tac att      869
Leu Asp Cys Ala Ile Pro Thr Gly Asn Ser Leu Val Glu Pro Tyr Ile
265                 270                 275                 280 gct ggc cac aac att ctt cta gcc cac gct gag gct gtt gat ctt tac      917
Ala Gly His Asn Ile Leu Leu Ala His Ala Glu Ala Val Asp Leu Tyr
                285                 290                 295 aac aag tat tac aag ggc gag aac ggc cgc ata ggt ctt gca ttt gat      965
Asn Lys Tyr Tyr Lys Gly Glu Asn Gly Arg Ile Gly Leu Ala Phe Asp
            300                 305                 310 gta atg ggt cgt gtg cca tac gga aca tca ttt cta gat gaa cag gcc     1013
Val Met Gly Arg Val Pro Tyr Gly Thr Ser Phe Leu Asp Glu Gln Ala
        315                 320                 325 aaa gaa agg tcc atg gac att aac cta gga tgg ttc ttg gag cct gtg     1061
Lys Glu Arg Ser Met Asp Ile Asn Leu Gly Trp Phe Leu Glu Pro Val
330                 335                 340 gtt cgt ggt gac tac ccc ttc tca atg aga tcg tta gcg agg gaa cga     1109
Val Arg Gly Asp Tyr Pro Phe Ser Met Arg Ser Leu Ala Arg Glu Arg
345                 350                 355                 360 cta ccc ttc ttc agt gac aaa cag caa gag aag ctt gtg gga tcc tat     1157
Leu Pro Phe Phe Ser Asp Lys Gln Gln Glu Lys Leu Val Gly Ser Tyr
                365                 370                 375 aac atg ttg gga ata aac tac tac acc tca ata ttc tcc aaa cat atc     1205
Asn Met Leu Gly Ile Asn Tyr Tyr Thr Ser Ile Phe Ser Lys His Ile
            380                 385                 390 gac atc tca cca aaa tac tcg cct gtt ctc aac act gac gac gcc tac     1253
Asp Ile Ser Pro Lys Tyr Ser Pro Val Leu Asn Thr Asp Asp Ala Tyr
        395                 400                 405 gct agt caa gaa acg tat ggg cct gac ggg aaa ccc att ggt cct cct     1301
Ala Ser Gln Glu Thr Tyr Gly Pro Asp Gly Lys Pro Ile Gly Pro Pro
410                 415                 420 atg gga aat ccg tgg atc tac tta tac cca gaa ggc cta aag gat atc     1349
Met Gly Asn Pro Trp Ile Tyr Leu Tyr Pro Glu Gly Leu Lys Asp Ile
425                 430                 435                 440 ctt atg atc atg aag aac aaa tat gga aac cca cct atc tac atc act     1397
Leu Met Ile Met Lys Asn Lys Tyr Gly Asn Pro Pro Ile Tyr Ile Thr
                445                 450                 455 gag aac gga atc ggg gat gtt gat aca aag gag aaa cct cta ccc atg     1445
Glu Asn Gly Ile Gly Asp Val Asp Thr Lys Glu Lys Pro Leu Pro Met
            460                 465                 470 gag gct gcc tta aat gac tac aaa agg cta gat tac atc cag cgc cac     1493
Glu Ala Ala Leu Asn Asp Tyr Lys Arg Leu Asp Tyr Ile Gln Arg His
        475                 480                 485 atc tca act ctc aag gag tca ata gac ttg gga gca aat gtg cat ggc     1541
Ile Ser Thr Leu Lys Glu Ser Ile Asp Leu Gly Ala Asn Val His Gly
490                 495                 500 tac ttc gct tgg tct ctg ctg gat aac ttt gaa tgg tac gcc ggc tac     1589
Tyr Phe Ala Trp Ser Leu Leu Asp Asn Phe Glu Trp Tyr Ala Gly Tyr
505                 510                 515                 520 acc gaa cgt tat ggc att gtc tac gtc gac cgc aaa aat aac tac acg     1637
Thr Glu Arg Tyr Gly Ile Val Tyr Val Asp Arg Lys Asn Asn Tyr Thr
                525                 530                 535 cgc tac atg aag gag tca gcc aag tgg tta aaa gag ttc aat act gcg     1685
Arg Tyr Met Lys Glu Ser Ala Lys Trp Leu Lys Glu Phe Asn Thr Ala
```

-continued

```
                540                 545                 550
aag aag cct agc aag aag att att acg cca gct taa aaacatggga          1731
Lys Lys Pro Ser Lys Lys Ile Ile Thr Pro Ala *
        555                 560 cctcgtgatg tgggtacggt gccacccatg aaataaaaac ctagtgtgtg gtttgaaacc   1791 taaattttc tttttctttt ttgcaccatg agagaggtag tggagtcata ttctccagca    1851
ccgtggctaa taatgtattg ttgcagtaca atctagcatt gtcgtcatgc aataaataaa   1911
gtgactggtt tccctatttc                                              1931
```

<210> SEQ ID NO 4
<211> LENGTH: 563
<212> TYPE: PRT
<213> ORGANISM: Zea mays

<400> SEQUENCE: 4

```
Met Ala Pro Leu Leu Ala Ala Met Asn His Ala Ala His Pro Val
 1               5                  10                  15

Leu Arg Ser His Leu Gly Pro Asn Asn Glu Ser Phe Ser Arg His His
             20                  25                  30

Leu Ser Ser Ser Pro Gln Ser Ser Lys Arg Arg Phe Asn Leu Ser Phe
         35                  40                  45

Thr Pro Arg Ser Ala Arg Val Gly Asn Gln Asn Gly Val Gln Leu Leu
     50                  55                  60

Ser Pro Ser Glu Ile Pro Arg Arg Asp Trp Phe Pro Ser Asp Phe Ile
65                  70                  75                  80

Phe Gly Ala Ala Thr Ser Ala Tyr Gln Ile Glu Gly Ala Trp Asn Glu
                 85                  90                  95

Asp Gly Lys Gly Glu Ser Asn Trp Asp His Phe Cys His Asn Phe Pro
            100                 105                 110

Glu Arg Ile Met Asp Gly Ser Asn Ala Asp Ile Gly Ala Asn Ser Tyr
        115                 120                 125

His Met Tyr Lys Thr Asp Val Arg Leu Leu Lys Glu Met Gly Met Asp
    130                 135                 140

Ala Tyr Arg Phe Ser Ile Ser Trp Pro Arg Ile Leu Pro Lys Gly Thr
145                 150                 155                 160

Val Glu Gly Gly Ile Asn Gln Asp Gly Ile Asp Tyr Tyr Lys Arg Leu
                165                 170                 175

Ile Asn Leu Leu Leu Glu Asn Gly Ile Glu Pro Tyr Val Thr Ile Phe
            180                 185                 190

His Trp Asp Val Pro Gln Ala Leu Glu Glu Lys Tyr Gly Gly Phe Leu
        195                 200                 205

Asp Lys Thr Gln Lys Arg Ile Val Asn Asp Tyr Lys Asn Phe Ala Lys
    210                 215                 220

Val Cys Phe Asp Asn Phe Gly Asp Lys Val Lys Asn Trp Leu Thr Phe
225                 230                 235                 240

Asn Glu Pro Gln Thr Phe Thr Ser Phe Ser Tyr Gly Thr Gly Val Phe
                245                 250                 255

Ala Pro Gly Arg Cys Ser Pro Gly Leu Asp Cys Ala Ile Pro Thr Gly
            260                 265                 270

Asn Ser Leu Val Glu Pro Tyr Ile Ala Gly His Asn Ile Leu Leu Ala
        275                 280                 285

His Ala Glu Ala Val Asp Leu Tyr Asn Lys Tyr Tyr Lys Gly Glu Asn
    290                 295                 300
```

-continued

```
Gly Arg Ile Gly Leu Ala Phe Asp Val Met Gly Arg Val Pro Tyr Gly
305                 310                 315                 320

Thr Ser Phe Leu Asp Glu Gln Ala Lys Glu Arg Ser Met Asp Ile Asn
            325                 330                 335

Leu Gly Trp Phe Leu Glu Pro Val Val Arg Gly Asp Tyr Pro Phe Ser
            340                 345                 350

Met Arg Ser Leu Ala Arg Glu Arg Leu Pro Phe Phe Ser Asp Lys Gln
            355                 360                 365

Gln Glu Lys Leu Val Gly Ser Tyr Asn Met Leu Gly Ile Asn Tyr Tyr
        370                 375                 380

Thr Ser Ile Phe Ser Lys His Ile Asp Ile Ser Pro Lys Tyr Ser Pro
385                 390                 395                 400

Val Leu Asn Thr Asp Asp Ala Tyr Ala Ser Gln Glu Thr Tyr Gly Pro
            405                 410                 415

Asp Gly Lys Pro Ile Gly Pro Pro Met Gly Asn Pro Trp Ile Tyr Leu
            420                 425                 430

Tyr Pro Glu Gly Leu Lys Asp Ile Leu Met Ile Met Lys Asn Lys Tyr
        435                 440                 445

Gly Asn Pro Pro Ile Tyr Ile Thr Glu Asn Gly Ile Gly Asp Val Asp
    450                 455                 460

Thr Lys Glu Lys Pro Leu Pro Met Glu Ala Ala Leu Asn Asp Tyr Lys
465                 470                 475                 480

Arg Leu Asp Tyr Ile Gln Arg His Ile Ser Thr Leu Lys Glu Ser Ile
            485                 490                 495

Asp Leu Gly Ala Asn Val His Gly Tyr Phe Ala Trp Ser Leu Leu Asp
            500                 505                 510

Asn Phe Glu Trp Tyr Ala Gly Tyr Thr Glu Arg Tyr Gly Ile Val Tyr
        515                 520                 525

Val Asp Arg Lys Asn Asn Tyr Thr Arg Tyr Met Lys Glu Ser Ala Lys
        530                 535                 540

Trp Leu Lys Glu Phe Asn Thr Ala Lys Lys Pro Ser Lys Lys Ile Ile
545                 550                 555                 560

Thr Pro Ala
```